(12) United States Patent
Peglion et al.

(10) Patent No.: US 8,076,325 B2
(45) Date of Patent: Dec. 13, 2011

(54) 1,2,4,5-TETRAHYDRO-3H-BENZAZEPINE COMPOUNDS, A PROCESS FOR THEIR PREPARATION AND PHARMACEUTICAL COMPOSITIONS CONTAINING THEM

(75) Inventors: Jean-Louis Peglion, Le Vesinet (FR); Bertrand Goument, Viroflay (FR); Aimee Dessinges, Rueil Malmaison (FR); Pascal Caignard, Epinay sur Seine (FR); Jean-Paul Vilaine, Chatenay Malabry (FR); Catherine Thollon, Paris (FR); Nicole Villeneuve, Rueil Malmaison (FR); Stefano Chimenti, Paris (FR)

(73) Assignee: Les Laboratoires Servier, Suresnes Cedex (FR)

( * ) Notice: Subject to any disclaimer, the term of this patent is extended or adjusted under 35 U.S.C. 154(b) by 31 days.

(21) Appl. No.: 12/283,110

(22) Filed: Sep. 9, 2008

(65) Prior Publication Data

US 2009/0069296 A1    Mar. 12, 2009

(30) Foreign Application Priority Data

Sep. 11, 2007 (FR) ..................... 07 06346

(51) Int. Cl.
*A01N 43/00* (2006.01)
*A61K 31/55* (2006.01)
*C07D 223/16* (2006.01)
(52) U.S. Cl. .................. 514/217.01; 540/594
(58) Field of Classification Search ............. 514/217.01; 540/594
See application file for complete search history.

(56) References Cited

U.S. PATENT DOCUMENTS

| 4,584,293 A | 4/1986 | Reiffen et al. |
| 6,514,964 B1 | 2/2003 | Chen et al. |

FOREIGN PATENT DOCUMENTS

| EP | 0161604 | 11/1985 |
| EP | 0534859 | 3/1993 |
| WO | 2006/092491 | 9/2006 |

OTHER PUBLICATIONS

Wickenden AD, Maher MP, Chaplan SR. HCN Pacemaker Channels and Pain: A Drug Discovery Perspective. Current Pharmaceutical Design. Jun. 2009: 15(6); 2149-2168.*
French Preliminary Search Report for FR/0706346 of May 6, 2008.

Kannel, et al., *American Heart Journal*, 1987, 113, 1489-1494.
Borer, et al., *Circulation*, 2003, 107, 817-823.
Diaz, et al., *European Heart Journal*, 2005, 26, 967-974.
Hjalmarson, et al., *American Journal of Cardiology*, 1990, 65, 547-553.
Mulder, et al., *Circulation*, 2004, 109, 1674-1679.
Beere, et al., *Science*, 1984, 226, 180-182.
Heidland, et al., *Circulation*, 2001, 104, 1477-1482.

* cited by examiner

*Primary Examiner* — San-Ming Hui
*Assistant Examiner* — Paul Zarek
(74) *Attorney, Agent, or Firm* — Hueschen and Sage

(57) ABSTRACT

Compounds of formula (I):

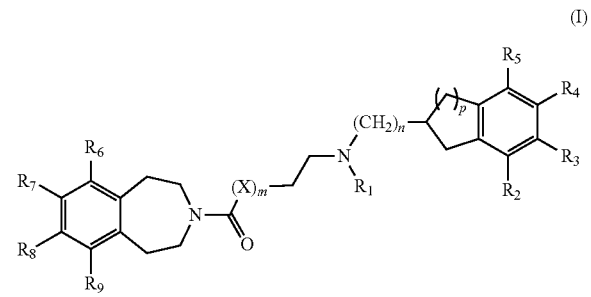

wherein:
$R_1$ represents a hydrogen atom or a group selected from cycloalkyl, benzyl and optionally substituted alkyl,
$R_2$, $R_3$, $R_4$ and $R_5$ each represent a hydrogen atom or a hydroxy, methyl, $-OSO_2R_{10}$, $-OCOR_{10}$ or optionally substituted alkoxy group, or $R_2$ and $R_3$, or $R_3$ and $R_4$, or $R_4$ and $R_5$ together form a group $-O-(CH_2)_q-O-$, $-O-CH=CH-O-$ or $-O-CH=CH-$,
$R_6$, $R_7$, $R_8$ and $R_9$ each represent a hydrogen atom or an alkoxy group, or $R_6$ and $R_7$, or $R_7$ and $R_8$, or $R_8$ and $R_9$ together form a group $-O-(CH_2)_q-O-$,
$R_{10}$ represents a group selected from linear or branched $C_1$-$C_6$alkoxy, $NR_{11}R'_{11}$ and optionally substituted alkyl,
$R_{11}$ and $R'_{11}$ each represent a hydrogen atom or an alkyl group, or $R_{11}$ and $R'_{11}$ together with the nitrogen atom carrying them form an optionally substituted, monocyclic or bicyclic, nitrogen-containing heterocycle,
X represents O, NH or $CH_2$,
m and p each represent 0 or 1,
n and q each represent 1 or 2,
in racemic form or in the form of optical isomers, and also addition salts thereof with a pharmaceutically acceptable acid.
Medicinal products containing the same which are useful in treating various pathologies.

14 Claims, No Drawings

1,2,4,5-TETRAHYDRO-3H-BENZAZEPINE COMPOUNDS, A PROCESS FOR THEIR PREPARATION AND PHARMACEUTICAL COMPOSITIONS CONTAINING THEM

The present invention relates to new 1,2,4,5-tetrahydro-3H-benzazepine compounds, to a process for their preparation and to pharmaceutical compositions containing them.

The compounds of the invention block HCN (hyperpolarisation-activated cyclic nucleotide-gated) channels.

The blocking of HCN channels caused by the compounds of the invention allows the latter to be used in curative and preventative treatments for any pathology in which the activity or expression of HCN channels is degraded and abnormal.

Said compounds of the invention may especially be useful in the curative or preventative treatment of pain, in particular neuropathic and inflammatory pain (Chaplan S R, Guo H Q, Lee D H, Luo L, Liu C, Kuei C, Velumian A A, Butler M P, Brown S M, Dubin A E. *Neuronal hyperpolarization-activated pacemaker channels drive neuropathic pain. J Neurosci* 2003; 23(4):1169-78; Luo L, Chang L, Brown S M, Ao H, Lee D H, Higuera E S, Dubin A E, Chaplan S R. *Role of peripheral hyperpolarization-activated cyclic nucleotide-modulated channel pacemaker channels in acute and chronic pain models in the rat. Neuroscience* 2007, 144(4):1477-85; Jiang Y Q, Sun Q, Tu H Y, Wan Y. *Characteristics of HCN Channels and Their Participation in Neuropathic Pain. Neurochem Res*. 2008 May 7), bladder overactivity (Stamatiou K, Heretis I, Skoumbourdis E. *Does ivabradine exhibit a role in the reduction of bladder overactivity? Int Urol Nephrol*. 2008 Feb. 1), and eye dryness sensations (Ingram S L, Williams J T. *Modulation of the hyperpolarization-activated current (Ih) by cyclic nucleotides in guinea-pig primary afferent neurons. J Physiol*. 1996; 492:97-106; Belmonte C. *Eye dryness sensations after refractive surgery: impaired tear secretion or "phantom" cornea? J Refract Surg* 2007; 23(6):598-602).

The compounds of the invention reduce cardiac pacemaker activity in direct and selective manner.

The selective reduction of heart rate caused by the compounds of the invention makes it possible for the latter to be used curatively or preventatively in the various pathologies in which accelerated heart rate acts as a trigger or has an aggravating role. Said compounds may especially improve the treatment and long-term prognosis of ischaemic cardiopathies (Dyer A R, Persky V, Stamler J, and al. *Heart rate as a prognostic factor for coronary heart disease and mortality: findings in three Chicago epidemiologic studies. Am J Epidemiol.* 1980; 112: 736-749; Kannel W B, Kannel C, Paffengarger R S Jr, and al. *Heart rate and cardiovascular mortality: the Framingham Study. Am Heart J.* 1987; 113: 1489-1494; Gillum R F, Makuc D M, Feldman J J. *Pulse rate, coronary heart disease, and death: the NHANES I epidemiologic follow-up study. Am Heart J.* 1991; 121: 172-177; Greenland P, Daviglus M L, Dyer A R, and al. *Resting heart rate is a risk factor for cardiovascular and noncardiovascular mortality: the Chicago Heart Association Detection Project in Industry. Am J Epidemiol* 1999; 149: 853-862; Kristal-Boneh E, Silber H, Harari G, and al. *The association of resting heart rate with cardiovascular, cancer and all-cause mortality. Eight year follow-up of 3527 male Israeli employees (the CORDIS Study). Eur Heart J* 2000; 21: 116-124; Palatini P. *Heart rate as a cardiovascular risk factor: do women differ from men? Ann Med.* 2001; 33: 213-221; Aronow W S, Ahn C, Mercando A D, and al. *Association of average heart rate on 24-hour ambulatory electrocardiograms with incidence of new coronary events at 48-month follow-up in 1,311 patients (mean age 81 years) with heart disease and sinus rhythm. Am J Cardiol.* 1996; 78: 1175-1176) in their various clinical manifestations: stable angina (Borer J S, Fox K, Jaillon P, and al. *Antianginal and antiischemic effects of ivabradine, an $I_f$ inhibitor, in stable angina. A randomized, double-blind, multicentered, placebo-controlled trial. Circulation* 2003; 107:817-23; Diaz A, Bourassa M G, Guertin M C, Tardif J C: *Long-term prognostic value of resting heart rate in patients with suspected or proven coronary artery disease. Eur Heart J* 2005; 26:967-974), unstable angina, myocardial infarction (Hjalmarson A, Gilpin E A, Kjekshus J, Schieman G, Nicod P, Henning H, Ross J Jr: *Influence of heart rate on mortality after acute myocardial infarction. Am J Cardiol* 1990; 65:547-553; Disegni E, Goldbourt U, Reicher-Reiss H, Kaplinsky E, Zion M, Boyko V, Behar S: *The predictive value of admission heart rate on mortality in patients with acute myocardial infarction. SPRINT Study Group. Secondary Prevention Reinfarction Israeli Nifedipine Trial. J Clin Epidemiol* 1995; 48:1197-1205; Zuanetti G, Mantini L, Hernandez-Bernal F, Barlera S, di Gregorio D, Latini R, Maggioni A P: *Relevance of heart rate as a prognostic factor in patients with acute myocardial infarction: insights from the GISSI-2 study. Eur Heart J* 1998; 19(suppl F):F19-F26; Lee K L, Woodlief L H, Topol E J, Weaver W D, Betriu A, Col J, Simoons M, Aylward P, Van de Werf F, Califf R M: *Predictors of 30-day mortality in the era of reperfusion for acute myocardial infarction. Results from an international trial of 41,021 patients. GUSTO-I Investigators. Circulation* 1995; 91:1659-1668; Steffenino G, Santoro G M, Maras P, Mauri F, Ardissino D, Violini R, Chiarella F. Lucci D, Marini M, Baldasseroni S, Maggioni A P: *In-hospital and one-year outcomes of patients with high-risk acute myocardial infarction treated with thrombolysis or primary coronary angioplasty. Ital Heart J* 2004; 5:136-145; Mauss O, Klingenheben T, Ptaszynski P, Hohnloser S H: *Bedside risk stratification after acute myocardial infarction: prospective evaluation of the use of heart rate and left ventricular function. J Electrocardiol* 2005; 38:106-112), post infarction; heart failure whether systolic or diastolic (Aaronson K D, Schwartz J S, Chen T M, Wong K L, Goin J E, Mancini D M: *Development and prospective validation of a clinical index to predict survival in ambulatory patients referred for cardiac transplant evaluation. Circulation* 1997; 95:2660-2667; CIBIS-II Investigators and Committees: *The cardiac Insufficiency Bisoprolol Study II (CIBIS-II): a randomised trial. Lancet* 1999; 353:9-13; Mulder P, Barbier S, Chagraoui A, and al. *Long-term heart rate reduction induced by the selective $I_f$ current inhibitor ivabradine improves left ventricular function and intrinsic myocardial structure in congestive heart failure. Circulation* 2004; 109: 1674-9); ventricular or supraventricular rhythm disturbances (James R, Arnold J, Allen J, and al. *The effects of heart rate, myocardial ischemia and vagal stimulation on the threshold of ventricular fibrillation. Circulation.* 1977; 55: 311-7; Bernier M, Curtis J M, Hearse D J. *Ischemia-induced and reperfusion-induced arrhythmias: importance of heart rate. Am J Physiol* 1989; 256: H21-H31), pathologies constituting a vascular risk factor: arterial hypertension, diabetes, hypercholesterolaemia, by reducing especially the development of atherosclerosis lesions and their complications (Beere P A, Glagov S, Zarins C K. *Retarding effect of lowered heart rate on coronary atherosclerosis. Science* 1984; 226: 180-2; Kaplan J R, Manuck S B, Clarkson T B. *The influence of heart rate on coronary atherosclerosis. J Cardiovasc Pharmacol* 1987; 10: S100-S102; Beere P A, Glagov S, Zarins C K. *Experimental atherosclerosis at the carotid bifurcation of the cynomolgus monkey. Localization, compensatory enlargement, and the sparing effect of lowered heart rate. Atheroscler Thromb* 1992; 12, 1245-53; Perski A, Hamsten A, Linvall K and al. *Heart rate correlates with severity of coronary artery atherosclerosis in young postinfarction patients. Am Heart J* 1988; 116: 1369-73; Perski A Ollson G, Landou C and al. *Minimum heart rate and coronary atherosclerosis: Independent relations to global severity and rate of progression of angiographic lesions in men with myocardial infarction at a young age. Am Heart J* 1992; 123: 609-16; Heidland U E, Strauer B E. *Left ventricular muscle mass and elevated heart rate are associated with coronary plaque disruption. Circulation.* 2001; 104: 1477-82).

Compounds reducing heart rate in direct and selective manner are known especially from the patent application EP 0 534 859.

The problem for the present invention was to obtain new compounds which reduce heart rate, which are simultaneously potent, selective and safe to use.

In this regard it is of value to have compounds which have few risks of drug interactions.

More specifically, the present invention relates to compounds of formula (I):

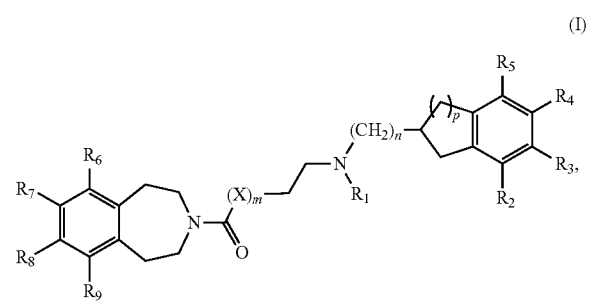

wherein:
- $R_1$ represents a hydrogen atom or a group selected from $C_3$-$C_7$cycloalkyl, benzyl and linear or branched $C_1$-$C_6$alkyl, the alkyl group being saturated or unsaturated and optionally substituted by a hydroxy or $C_3$-$C_7$cycloalkyl group or by one or more halogen atoms,
- $R_2$, $R_3$, $R_4$ and $R_5$, which may be the same or different, each represent a hydrogen atom or a hydroxy group; methyl group; —$OSO_2R_{10}$ group; —$OCOR_{10}$ group; or linear or branched, saturated or unsaturated $C_1$-$C_6$alkoxy group optionally substituted by a methoxy or —(CO)—$NR_{12}R'_{12}$ group; or $R_2$ and $R_3$, or $R_3$ and $R_4$, or $R_4$ and $R_5$ together form a group —O—$(CH_2)_q$—O—, —O—CH=CH—O— or —O—CH=CH—,
- $R_6$, $R_7$, $R_8$ and $R_9$, which may be the same or different, each represent a hydrogen atom or a linear or branched, saturated or unsaturated $C_1$-$C_6$alkoxy group, or $R_6$ and $R_7$, or $R_7$ and $R_8$, or $R_8$ and $R_9$ together form a group —O—$(CH_2)_q$—O—,
- $R_{10}$ represents a group selected from linear or branched $C_1$-$C_6$alkoxy, $NR_{11}R'_{11}$ and linear or branched $C_1$-$C_6$alkyl which is optionally substituted by one or more halogen atoms,
- $R_{11}$ and $R'_{11}$, which may be the same or different, each represent a hydrogen atom or a linear or branched $C_1$-$C_6$alkyl group, or $R_{11}$ and $R'_{11}$ together with the nitrogen atom carrying them form a monocyclic or bicyclic, 5- to 8-membered, nitrogen-containing heterocycle optionally containing another hetero atom selected from O and N, said heterocycle being optionally substituted by one or more halogen atoms,
- $R_{12}$ and $R'_{12}$, which may be the same or different, each represent a hydrogen atom or a linear or branched $C_1$-$C_6$alkyl group,
- X represents O, NH or $CH_2$,
- m and p, which may be the same or different, each represent 0 or 1,
- n and q, which may be the same or different, each represent 1 or 2, to their optical isomers when they exist, and also to addition salts thereof with a pharmaceutically acceptable acid.

Among the pharmaceutically acceptable acids there may be mentioned without implying any limitation hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid, pamoic acid, 1,5-naphthalenedisulphonic acid.

One aspect of the present invention relates to compounds of formula (I) wherein $R_1$ represents a hydrogen atom or a linear or branched $C_1$-$C_6$alkyl group, to their optical isomers when they exist, and also to addition salts thereof with a pharmaceutically acceptable acid.

Another aspect of the invention relates to compounds of formula (I) wherein $R_1$ represents a $C_3$-$C_7$cycloalkyl group or a cycloalkylalkyl group wherein the cycloalkyl moiety contains from 3 to 7 carbon atoms and the alkyl moiety contains from 1 to 6 carbon atoms and is linear or branched, to their optical isomers when they exist, and also to addition salts thereof with a pharmaceutically acceptable acid.

Another aspect of the invention relates to compounds of formula (I) wherein $R_2$, $R_3$, $R_4$ and $R_5$, which may be the same or different, each represent a hydrogen atom or a linear or branched, saturated or unsaturated $C_1$-$C_6$alkoxy group or —$OCOR_{10}$ wherein $R_{10}$ represents a group $NR_{11}R'_{11}$ as defined hereinbefore, to their optical isomers when they exist, and also to addition salts thereof with a pharmaceutically acceptable acid.

Preferably, $R_{11}$ and $R'_{11}$ each represent a linear or branched $C_1$-$C_6$alkyl group.

Another aspect of the invention relates to compounds of formula (I) wherein $R_6$, $R_7$, $R_8$ and $R_9$, which may be the same or different, each represent a hydrogen atom or a linear or branched, saturated or unsaturated $C_1$-$C_6$alkoxy group, to their optical isomers when they exist, and also to addition salts thereof with a pharmaceutically acceptable acid.

Another aspect of the invention relates to compounds of formula (I) wherein m represents 0, to their optical isomers when they exist, and also to addition salts thereof with a pharmaceutically acceptable acid.

Another aspect of the invention relates to compounds of formula (I) wherein m represents 1 and X represents $CH_2$, to their optical isomers when they exist, and also to addition salts thereof with a pharmaceutically acceptable acid.

Another aspect of the invention relates to compounds of formula (I) wherein p represents 0, to their optical isomers when they exist, and also to addition salts thereof with a pharmaceutically acceptable acid.

Another aspect of the invention relates to compounds of formula (I) wherein p represents 1, to their optical isomers when they exist, and also to addition salts thereof with a pharmaceutically acceptable acid.

Another aspect of the invention relates to the compounds wherein $R_1$ represents a hydrogen atom or a linear or branched $C_1$-$C_6$alkyl group, $R_2$, $R_3$, $R_4$ and $R_5$, which may be the same or different, each represent a hydrogen atom or a linear or branched, saturated or unsaturated $C_1$-$C_6$alkoxy group, $R_6$, $R_7$, $R_8$ and $R_9$, which may be the same or different, each represent a hydrogen atom or a linear or branched, saturated or unsaturated $C_1$-$C_6$alkoxy group, m represents 0, n represents 1 and p represents 0, to their optical isomers, and also to addition salts thereof with a pharmaceutically acceptable acid.

Another aspect of the invention relates to the following compounds:

N-{[3,4-dimethoxybicyclo[4.2.0]octa-1,3,5-trien-7-yl]methyl}-3(7,8-dimethoxy-1,2,4,5-tetrahydro-3H-3-benzazepin-3-yl)-N-methyl-3-oxopropan-1-amine, its optical isomers, and also addition salts thereof with a pharmaceutically acceptable acid;

N-{[3,4-dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine, its optical isomers, and also addition salts thereof with a pharmaceutically acceptable acid;

N-[2-(5,6-dimethoxy-2,3-dihydro-1H-inden-2-yl)methyl]-3-(7,8-dimethoxy-1,2,4,5-tetrahydro-3H-3-benzazepin-3-yl)-3-oxopropan-1-amine, and also addition salts thereof with a pharmaceutically acceptable acid;

N-{[3,4-dimethoxybicyclo[4.2.0]octa-1,3,5-trien-7-yl]methyl}-3-(7,8-dimethoxy-1,2,4,5-tetrahydro-3H-3-benzazepin-3-yl)-N-methyl-4-oxobutan-1amine, its optical isomers, and also addition salts thereof with a pharmaceutically acceptable acid;

N-{[3,4-dimethoxybicyclo[4.2.0]octa-1,3,5-trien-7-yl]methyl}-3-(7,8-dimethoxy-1,2,4,5-tetrahydro-3H-3-benzazepin-3-yl)-4-oxobutan-1-amine, its optical isomers, and also addition salts thereof with a pharmaceutically acceptable acid;

7-{[[3-(7,8-dimethoxy-1,2,4,5-tetrahydro-3H-3-benzazepin-3-yl)-3-oxopropyl]-(methyl)amino]methyl}bicyclo[4.2.0]octa-1,3,5-trien-3-yl dimethylcarbamate, its optical isomers, and also addition salts thereof with a pharmaceutically acceptable acid.

The present invention relates also to a process for the preparation of compounds of formula (I), starting from a compound of formula (II):

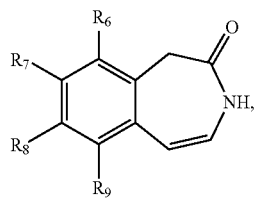

(II)

wherein $R_6$, $R_7$, $R_8$ and $R_9$ are as defined for formula (I), which is subjected to a hydrogenation reaction to yield the compound of formula (III):

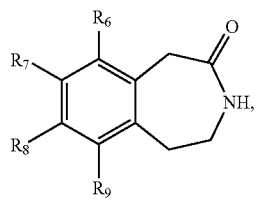

(III)

wherein $R_6$, $R_7$, $R_8$ and $R_9$ are as defined hereinbefore, which is reduced to yield the compound of formula (IV):

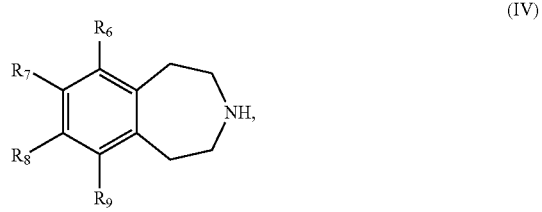

(IV)

wherein $R_6$, $R_7$, $R_8$ and $R_9$ are as defined hereinbefore, which is reacted either, when it is desired to obtain compounds of formula (I) wherein m represents zero, with acryloyl chloride to yield the compound of formula (V):

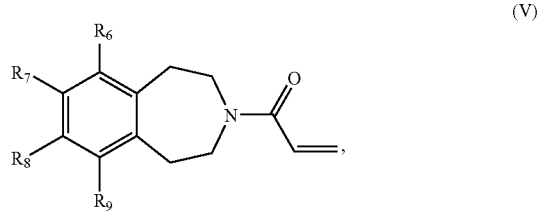

(V)

wherein $R_6$, $R_7$, $R_8$ and $R_9$ are as defined hereinbefore, which is subjected to a coupling reaction with a compound of formula (VI):

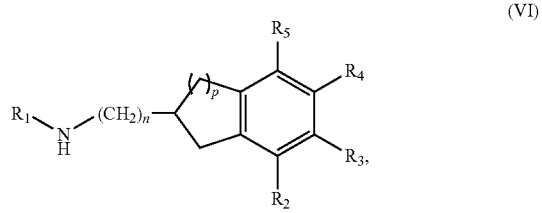

(VI)

wherein n, p, $R_1$, $R_2$, $R_3$, $R_4$ and $R_5$ are as defined for formula (I), to yield the compounds of formula (Ia), a particular case of compounds of formula (I) wherein m represents zero:

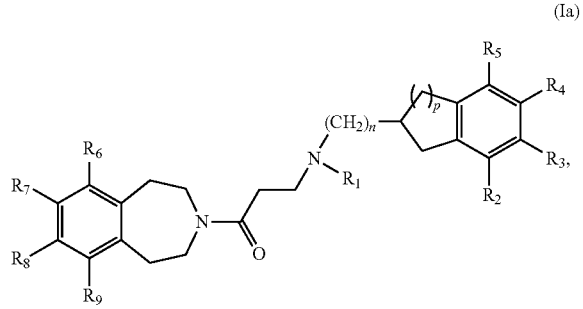

(Ia)

wherein n, p, $R_1$, $R_2$, $R_3$, $R_4$, $R_5$, $R_6$, $R_7$, $R_8$ and $R_9$ are as defined for formula (I), or, when it is desired to obtain compounds of formula (I) wherein (X)m represents O or NH, with diphosgene to yield the compound of formula (VII):

(VII)

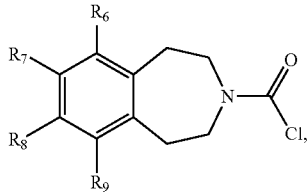

wherein $R_6$, $R_7$, $R_8$ and $R_9$ are as defined hereinbefore, which is reacted with a compound of formula (VIII):

(VIII)

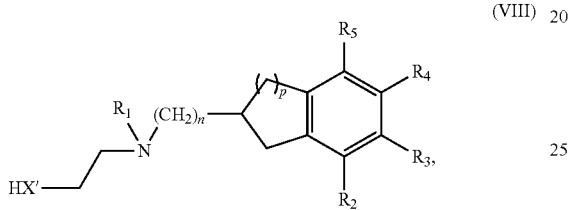

wherein n, p, $R_1$, $R_2$, $R_3$, $R_4$ and $R_5$ are as defined for formula (I) and X' represents O or NH, to yield the compounds of formula (Ib), a particular case of compounds of formula (I) wherein m represents 1 and X represents O or NH:

(Ib)

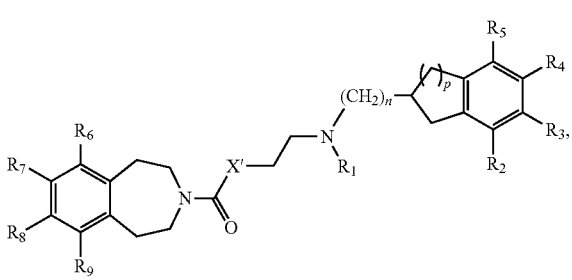

wherein n, p, $R_1$, $R_2$, $R_3$, $R_4$, $R_5$, $R_6$, $R_7$, $R_8$ and $R_9$ are as defined for formula (I) and X' represents O or NH, or, when it is desired to obtain compounds of formula (I) wherein $(X)_m$ represents $CH_2$, with gamma-butyrolactone to yield the compound of formula (IX):

(IX)

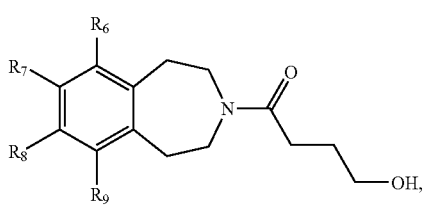

wherein $R_6$, $R_7$, $R_8$ and $R_9$ are as defined hereinbefore, which is oxidised to form the compound of formula (X):

(X)

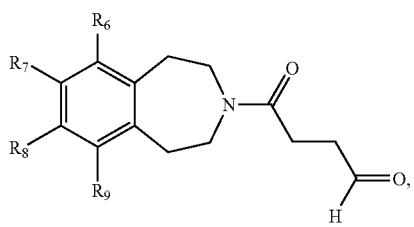

wherein $R_6$, $R_7$, $R_8$ and $R_9$ are as defined hereinbefore, which is reacted with a compound of formula (VI) to yield the compounds of formula (Ic), a particular case of compounds of formula (I) wherein m represents 1 and X represents $CH_2$:

(Ic)

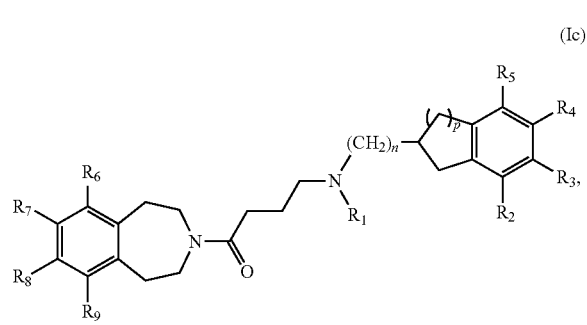

wherein n, p, $R_1$, $R_2$, $R_3$, $R_4$, $R_5$, $R_6$, $R_7$, $R_8$ and $R_9$ are as defined for formula (I).

The optically active forms of the compounds of formula (I) are obtained, either by starting from optically active forms of the synthesis intermediates of formulae (VI) and (VIII) or by resolving racemic forms of the compounds of formula (I), in accordance with methods known from the literature.

The compounds of the invention block HCN (hyperpolarisation-activated cyclic nucleotide-gated) channels.

The blocking of HCN channels caused by the compounds of the invention allows the latter to be used in curative or preventative treatments for any pathology in which the activity or expression of HCN channels is degraded and abnormal.

Said compounds of the invention may especially be useful in the curative or preventative treatment of pain, in particular neuropathic and inflammatory pain, bladder overactivity, and eye dryness sensations.

The compounds of the invention reduce cardiac pacemaker activity in direct and selective manner.

The selective reduction of heart rate caused by the compounds of the invention makes it possible for the latter to be used curatively or preventatively in the various pathologies in which accelerated heart rate acts as a trigger or has an aggravating role. Said compounds may especially improve the treatment and long-term prognosis of ischaemic cardiopathies in their various clinical manifestations: stable angina, acute coronary syndromes: unstable angina, threat syndromes and myocardial infarction, post infarction; heart failure whether systolic or diastolic and whether in the chronic or acute forms thereof; ventricular or supraventricular rhythm disturbances, pathologies constituting a vascular risk factor: arterial hypertension, diabetes, hypercholesterolaemia, especially by reducing endothelial dysfunction, the development of atherosclerosis lesions and their complications. Said compounds may make it possible to ensure myocardial protection in patients at risk, in the course of surgery or during septic shock. Reducing heart rate may moreover form part of the treatment of diseases such as hyperthyroidism accompanied by sinus tachycardia.

The present invention relates also to pharmaceutical compositions comprising as active ingredient a compound of formula I, or an addition salt thereof with a pharmaceutically acceptable acid, in combination with one or more pharmaceutically acceptable, inert, non-toxic excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, and especially tablets or dragees, sublingual tablets, hard gelatin capsules, capsules, suppositories, creams, ointments, dermal gels, injectable or drinkable preparations, aerosols, eye drops and nose drops.

In addition to the compound of formula (I), the pharmaceutical compositions according to the invention comprise one or more excipients or carriers such as diluents, lubricants, binders, disintegrating agents, absorbents, colourants, sweeteners.

By way of example of excipients or carriers, there may be mentioned:
- as diluents: lactose, dextrose, sucrose, mannitol, sorbitol, cellulose, glycerol,
- as lubricants: silica, talc, stearic acid and its magnesium and calcium salts, polyethylene glycol,
- as binders: aluminium silicate, magnesium silicate, starch, gelatin, tragacanth, methylcellulose, sodium carboxymethylcellulose and polyvinylpyrrolidone,
- as disintegrating agents: agar, alginic acid and its sodium salt, effervescent mixtures.

The percentage of active ingredient of formula (I) in the pharmaceutical composition is preferably from 5% to 50% by weight.

The useful dosage varies according to the age and weight of the patient, the administration route, the nature and severity of the disorder, and the administration of any associated treatments and ranges from 0.5 mg to 500 mg per day in one or more administrations.

The Examples that follow illustrate the present invention. The structures of the compounds described in the Examples were determined according to customary spectrophotometric techniques (infra-red, nuclear magnetic resonance, mass spectrometry).

The Preparations describe the preparation of intermediates of synthesis.

Abbreviations:
BINAP 2,2'-bis(diphenylphosphino)-1,1'-binaphthyl
TLC thin-layer chromatography
DMF N,N-dimethylformamide
DMSO dimethyl sulphoxide
eq. equivalent
IR infra-red
PEG 300 polyethylene glycol having an average molecular weight of 300 g/mol
THF tetrahydrofuran Preparation 1: [(4,5-Dimethoxybicyclo[4.2.0]octa-1,3,5-trien-7-yl)-methyl]-amine Step 1: 8,8-Diethoxy-2,3-dimethoxybicyclo[4.2.0]octa-1,3,5-triene 24 g (107 mmol) of bromoveratrol is poured onto 8.4 g (215 mmol)/2 eq. of sodium amide in 10 mL of toluene, followed by 25 g (215 mmol/2 eq.) of 1,1diethoxyethylene. Heating is carried out at 80° C. for 4 hours 30 minutes; cooling to −10° C. is carried out and 50 mL of water and then 50 mL of toluene are poured in. The phases are separated and the aqueous phase is extracted again with toluene. The combined toluene phases are washed with water to neutral pH and are then concentrated. The residue is chromatographed over 600 g of silica (eluant: dichloromethane) to yield the desired product.

Step 2: 4,5-Dimethoxybicyclo[4.2.0]octa-1,3,5-trien-7-one

To 7.5 g (29.7 mmol) of the preceding compound dissolved in 120 mL of THF, there are added 30 mL of 1M aqueous hydrochloric acid solution. Stirring is carried out at ambient temperature for 19 hours and then the maximum amount of THF is evaporated off. The white mass obtained is taken up in 150 mL of water and stirred for 1 hour at 5° C. After filtration, 3 washings with 15 mL of water and drying in vacuo, the desired product is collected.

Step 3: 4,5-Dimethoxybicyclo[4.2.0]octa-1,3,5-trien-7-ol

To 4.73 g (26.5 mmol) of the preceding compound suspended in 138 mL of methanol at 0° C. there is added, twice, over 5 minutes, 1.21 g (31.8 mmol) of sodium borohydride. After stirring for 1 hour at 0° C., the mixture is poured into 350 mL of water and then extracted 3 times with 100 mL of dichloromethane. The combined organic phases are washed twice with 50 mL of water, and then dried over magnesium sulphate and concentrated to yield the desired product.

Step 4: 8-Bromo-2,3-dimethoxybicyclo[4.2.0]octa-1,3,5-triene 4.55 g (25.3 mmol) of the preceding compound, 11.9 g (45.5 mmol/1.8 eq.) of triphenylphosphine and 10.05 g (30.3 mmol/1.2 eq.) of tetrabromomethane in 150 mL of ether are heated at reflux for 2 hours 30 minutes. After cooling, the insoluble material is filtered through a frit and rinsed 5 times with 50 mL of ether. After concentration of the filtrates, the residue is chromatographed over 550 g of silica (eluant: dichloromethane) to yield the desired product.

Step 5: 4,5-Dimethoxybicyclo[4.2.0]octa-1,3,5-triene-7-carbonitrile 6.0 g (24.8 mmol) of the preceding compound and 8.64 g (32.2 mmol/1.3 eq.) of tetrabutylammonium cyanide in 125 mL of THF are stirred at ambient temperature for 21 hours. After concentration of the reaction mixture, the residue is chromatographed over 350 g of silica (eluant: dichloromethane) to yield the desired product.

Step 6: [(4,5-Dimethoxybicyclo[4.2.0]octa-1,3,5-trien-7-yl)methyl]amine

To 4.01 g (21.2 mmol) of the preceding compound dissolved in 60 mL of methanol and 60 mL of 7N ammoniacal methanol there are added 2 mL of Raney nickel. Hydrogenation is carried out at ambient temperature and ordinary pressure for 6 hours 30 minutes. The mixture is then filtered over Celite, rinsed with methanol and concentrated to yield the desired product.

Preparation 2: [(2-Methoxybicyclo[4.2.0]octa-1,3,5-trien-7-yl)methyl]amine

Step 1: 3-(2,6-Dibromophenyl)-2-chloro-propanenitrile

To 62.4 g (464 mmol/1.2 eq.) of cupric chloride, 76 mL (580 mmol/1.5 eq.) of tert-butyl nitrite and 483 mL (7.34 moles/19 eq.) of acrylonitrile in 475 mL of acetonitrile, at ambient temperature, there is poured, dropwise, over 1 hour, 100 g (386 mmol) of 2,6-dibromoaniline dissolved in 380 mL of acetonitrile. Stirring is carried out for a further 1 hour at ambient temperature, and then the reaction mixture is poured into 1 liter of 20% aqueous hydrochloric acid solution. The aqueous phase is extracted with toluene and the combined toluene phases are washed with aqueous saturated sodium chloride solution. After concentration, the desired product is obtained and used as such in the following Step.

Step 2: 3-(2,6-Dibromophenyl)-propanenitrile

The preceding compound is dissolved in 1400 mL of acetic acid. 68 g (1.04 moles/2.7 eq.) of powdered zinc are added all at once. An exotherm to 58° C. develops slowly. After 1 hour in contact, the reaction mixture is poured onto 3 kg of ice. The aqueous phase obtained is extracted with 1 liter and then 500 mL of toluene. The combined toluene phases are washed with aqueous saturated sodium chloride solution. After concentration, the residue is chromatographed over silica to yield the desired product.

Step 3: 2-Bromobicyclo[4.2.0]octa-1,3,5-triene-7-carbonitrile 138 g (477 mmol) of the preceding compound in solid form are added to sodium amide (1.91 moles/4 eq.) in 3 liters of liquid ammonia. After stirring for 2 hours at the reflux of the ammonia, the reaction is stopped by adding 102 g (4 eq.) of solid ammonium chloride and then the ammonia is allowed to evaporate off. The residue is taken up in 1 liter of ether and stirred; the solid is filtered off and rinsed with ether. After concentration of the combined filtrates, the residue is chromatographed over 2 kg of silica (eluant: dichloromethane) to yield the desired product.

Step 4: 2-Bromobicyclo[4.2.0]octa-1,3,5-triene-7-carboxylic acid

To 75 g (360 mmol) of the preceding compound in 375 mL of ethanol, at ambient temperature, there is added a solution of 38 g (612 mmol: 1.7 eq.) of potassium hydroxide dissolved in 125 mL of water. Refluxing is carried out for 16 hours, and then the ethanol is evaporated off. 1 liter of water is added, the aqueous phase is washed twice with 250 mL of ether, and then acidification to pH 1 is carried out using concentrated hydrochloric acid. The precipitate formed is filtered off, rinsed with water and dried to yield the desired product.

Step 5: 2-(2-Bromobicyclo[4.2.0]octa-1,3,5-trien-7-yl)-4,4-dimethyl-4,5-dihydrooxazole 79 g (348 mmol) of the preceding compound and 39 g (417 mmol/1.2 eq.) of 1,1-dimethyl-2-hydroxyethylamine in 800 mL of xylene are mixed together. The mixture is heated at 140° C. for 6 hours, carrying out azeotropic entrainment of water. The mixture is then allowed to cool and stirring at ambient temperature is maintained overnight. The precipitate which is formed (essentially the starting acid) is filtered off and washed with toluene. The combined filtrates are concentrated to yield the desired product.

Step 6: [7-(4,4-Dimethyl-4,5-dihydro-1,3-oxazol-2-yl)bicyclo[4.2.0]octa-1,3,5-trien-2-yl-(diphenylmethylene)amine At ambient temperature, 48 g (171 mmol) of the preceding compound, 37.3 g (205 mmol/1.2 eq.) of benzophenone-imine, 1.57 g (1.71 mmol/0.01 eq.) of di-palladium tris (dibenzylidene-acetone), 3.2 g (5.14 mmol/0.03 eq.) of BINAP and 23 g (240 mmol/1.4 eq.) of sodium tert-butylate are mixed into 800 mL of toluene. Heating at 85° C. is carried out for 24 hours, adding 9.3 g (0.3 eq.) of benzophenone-imine after 4 hours. After stopping heating, the insoluble material is filtered off at about 50° C., and the filtrate is then concentrated to obtain the desired product, which is used as such in the next Step.

Step 7: 2-Aminobicyclo[4.2.0]octa-1,3,5-triene-7-carboxylic acid ethyl ester 117 g (about 171 mmol) of the preceding compound in 2400 mL of ethanol containing 200 mL of concentrated sulphuric acid are refluxed for 1 hour 30 minutes. The solvent is concentrated to the maximum and the material is taken up in 1.5 liters of water. The aqueous phase is washed with ether, made basic using sodium potassium carbonate and then extracted with ether. After drying over magnesium sulphate and concentration of the combined ethereal phases, the desired product is collected.

Step 8: 2-Hydroxybicyclo[4.2.0]octa-1,3,5-triene-7-carboxylic acid

In the cold state, 18.6 mL (345 mmol/6 eq.) of concentrated sulphuric acid are poured into 11 g (57.5 mmol) of the preceding compound suspended in 220 mL of water, whilst maintaining the temperature below 15° C. Cooling to about from 0 to 5° C. is carried out and, over 15 minutes, a solution of 4.36 g (63.3 mmol/1.1 eq.) of sodium nitrite in 25 mL of water is poured in dropwise; stirring is carried out for 5 minutes at 0° C. and then, over 10 minutes and whilst maintaining the temperature below 10° C., a solution of 144 mg (0.57 mmol/0.01 eq.) of copper sulphate pentahydrate in 166 mL of 1M aqueous sulphuric acid is poured in dropwise. Heating at 80° C. is then carried out for 1 hour and then stirring is carried out overnight at ambient temperature. The aqueous phase is extracted with ether, the combined ethereal phases are washed with an aqueous saturated sodium chloride solution, dried over magnesium sulphate and concentrated. The residue is chromatographed over 500 g of silica (eluant: dichloromethane/ethanol: 90/10) to yield the desired product.

Step 9: 2-Methoxybicyclo[4.2.0]octa-1,3,5-triene-7-carboxylic acid ethyl ester 6 g (33 mmol) of the preceding compound and 2.7 g (8.3 mmol/0.25 eq.) of caesium carbonate in 330 mL of dimethyl carbonate are heated at 130° C. for 45 hours. After filtration and concentration of the reaction mixture, the desired product is collected.

Step 10: 2-Methoxybicyclo[4.2.0]octa-1,3,5-triene-7-carboxamide

To 6 g (31 mmol) of the preceding compound in 50 mL of THF at 0° C. there are added, dropwise, 120 mL of 28% ammonium hydroxide. Stirring is carried out at ambient temperature for 2 days, and then the THF is evaporated off to the maximum. The aqueous phase is extracted with ethyl acetate. The combined organic phases are dried over magnesium sulphate and concentrated to yield the desired product.

Step 11: 1-(2-Methoxybicyclo[4.2.0]octa-1,3,5-trien-7-yl)methanamine 1.39 mL (14.7 mmol/3 eq.) of borane-dimethylsulphide are poured, dropwise, over 10 minutes, into 0.87 g (4.9 mmol) of the preceding compound dissolved in 20 mL of THF, at ambient temperature, and then heating at 70° C. is carried out for 24 hours. The mixture is brought back to ambient temperature, subjected to solvolysis using 7.5 mL of anhydrous methanol and heated again at reflux for 1 hour. After evaporation, the residue (0.99 g) is chromatographed on a column of 50 g of silica (eluant: dichloromethane/ethanol/ammonia: 95/5/0.5) to yield a first fraction of the desired product and another fraction of the same product in the form of boron complexes. That latter fraction, after treatment with ethanolic HCl, and then acid-base extraction, provides an additional fraction of the desired product.

Preparation 3:
7-(Aminomethyl)bicyclo[4.2.0]octa-1,3,5-trien-3-ol

Step 1: 3-Hydroxybicyclo[4.2.0]octa-1,3,5-triene-7-carbonitrile 68.7 g (431.6 mmol) of 3-methoxybicyclo[4.2.0]octa-1,3,5-triene-7-carbonitrile dissolved in 1500 mL of dichloromethane are brought to 0° C. There are then added, dropwise, over 1 hour 15 minutes, 863 mL of a 1M solution of boron tribromide in dichloromethane (863 mmol/2 eq.). The mixture is then allowed to come back up to ambient temperature overnight. The mixture is brought back to about 0° C. and is poured onto 1 kg of ice. Stirring is carried out for 30 minutes at ambient temperature, the phases are separated and the aqueous phase is extracted again twice with 500 mL of dichloromethane. The combined organic phases are washed with 600 mL of water and then dried over magnesium sulphate. After filtration and concentration, the desired product is obtained.

Step 2:
7-(Aminomethyl)bicyclo[4.2.0]octa-1,3,5-trien-3-ol

To 8.0 g (55.1 mmol) of the preceding nitrile dissolved in 170 mL of methanol and 170 mL of 7N ammoniacal methanol there are added 8 mL of Raney nickel. Hydrogenation is carried out at ambient temperature and ordinary pressure until the theoretical volume of hydrogen has been absorbed. The mixture is then filtered over Celite, rinsing with methanol, and is concentrated to obtain the desired amine.

Preparation 4:
8-(Aminomethyl)bicyclo[4.2.0]octa-1,3,5-trien-3-ol

The procedure is the same as for the product of Preparation 3, but starting from 4-methoxybicyclo[4.2.0]octa-1,3,5-triene-7-carbonitrile.

Preparation 5: [(3-Ethoxybicyclo[4.2.0]octa-1,3,5-trien-7-yl)methyl]amine

Step 1: 3-Ethoxybicyclo[4.2.0]octa-1,3,5-trien-7-carbonitrile 1.5 g (10.19 mmoles) of the product of Step 1 of Preparation 3 are dissolved in 15 mL of dimethylformamide (DMF).

2.8 g (2 equivalents) of potassium carbonate, and then 2.3 mL (3 equivalents) of ethyl bromide and 100 mg (0.06 of an equivalent) of potassium iodide are added. The reaction mixture is heated at 80° C. for 3 hours. Cooling is then carried out and the DMF is evaporated off using a rotary evaporator. The residue obtained is taken up in water and extracted with dichloromethane ($CH_2Cl_2$). The organic phase is dried over $MgSO_4$, filtered and then evaporated to yield 1.8 g of oil.

The oil is purified by flash chromatography over 100 g of silica (eluant: $CH_2Cl_2$ 100%) to yield the expected product, which crystallises at ambient temperature.

Melting point=50-52° C.

Step 2: [(3-Ethoxybicyclo[4.2.0]octa-1,3,5-trien-7-yl)methyl]amine 1.5 g (8.65 mmoles) of the product of Step 1 are dissolved in 30 mL of methanol (MeOH). 30 mL of a (7N) ammoniacal methanol solution and 0.5 g of Raney nickel. The reaction mixture is then hydrogenated overnight under a pressure of 1 bar, at ambient temperature. The catalyst is then filtered off and the filtrate is evaporated to dryness. The expected product is obtained in the form an oil.

Preparation 6: [(3-tert-Butoxybicyclo[4.2.0]octa-1,3,5-trien-7-yl)methyl]amine

Step 1: 3-tert-Butoxybicyclo[4.2.0]octa-1,3,5-triene-7-carbonitrile 2.0 g (13.59 mmoles) of the product of Step 1 of Preparation 3 are dissolved in 100 mL of dichloromethane ($CH_2Cl_2$). Cooling to 0° C. is carried out and isobutene is bubbled through the solution until it is saturated. 0.2 mL of concentrated sulphuric acid is then added and stirring at ambient temperature is carried out for 24 hours. The solution is neutralised by addition of NaOH (1N). Extraction with $CH_2Cl_2$, washing with water and drying over $MgSO_4$ are carried out, followed by filtration and evaporation of the filtrate to dryness. A residue is obtained which is purified by flash chromatography over 150 g of silica (eluant $CH_2Cl_2$ 100%) to yield the expected product in the form of an oil.

Step 2: [(3-tert-Butoxybicyclo[4.2.0]octa-1,3,5-trien-7-yl)methyl]amine 1.1 g (5.46 mmoles) of the product of Step 1 are dissolved in 30 mL of methanol (MeOH). 30 mL of (7N) ammoniacal methanol solution and 0.5 g of Raney nickel are added. The reaction mixture is hydrogenated overnight under a pressure of 1 bar, at ambient temperature. The catalyst is then filtered off and the filtrate is evaporated to dryness. The expected product is obtained in the form of an oil.

Preparation 7: 5,6-Dihydrocyclobuta[f][1,3]benzodioxol-5-ylmethylamine

Step 1: Ethyl(5,6-Dihydrocyclobuta[4,5]benzo[1,2-d][1,3]dioxol-5-yl-methyl)carbamate 7.9 g (44.6 mmoles) of (5,6-dihydrocyclobuta[4,5]benzo[1,2-d][1,3]dioxol-5-ylmethyl)amine are dissolved in 80 mL of dichloromethane. 80 mL of water and 6 mL (1.6 equivalents) of (12N) aqueous sodium hydroxide solution are added. Over 15 minutes there are added 3.95 mL (1.1 equivalents) of ethyl chloroformate and stirring is carried out at 25° C. for 2 hours. The mixture is separated and the organic phases is washed with saturated aqueous NaHCO₃ solution. Drying over MgSO₄, filtration and evaporation to dryness are carried out. The expected product is obtained in the form of a brown solid.

Step 2: 5,6-Dihydrocyclobuta[f][1,3]benzodioxol-5-ylmethylamine 7.5 g (30 mmoles) of the product of Step 1 are dissolved in 15 mL of anhydrous tetrahydrofuran. The solution is poured dropwise into a suspension comprising 1.48 g (1.3 equivalents) of AlLiH₄ suspended in 38 mL of anhydrous tetrahydrofuran. Stirring is carried out at 25° C. for 2 hours. The mixture is hydrolysed in the cold state using 2.7 mL of water, 2.7 mL of NaOH (20%) and then 2.7 mL of water. Filtration and evaporation of the filtrate to dryness are carried out. There are obtained 2.4 g of a residue which is purified by column chromatography over silica (eluant: CH₂Cl₂/ethanol/NH₄OH: 95/5/0.5. The expected product is obtained in the form of a brown oil.

Preparation 8: [2-(5,6-Dimethoxy-2,3-dihydro-1H-inden-2-yl)ethyl]amine 5 g (2.3 mmoles) of (5,6-dimethoxy-2,3-dihydro-1H-inden-2-yl)acetonitrile are dissolved in 50 ml of methanol. 50 mL of a (7N) MeOH—NH₃ solution and 0.5 g of Raney nickel are then added. Hydrogen is carried out for 4 days under a pressure of 5 bar, at 25° C. Filtration over Celite and evaporation of the filtrate to dryness are carried out. The residue is taken up in 50 mL of HCl (1N) and washed with ethyl acetate; the aqueous phase is then brought to pH=10 by adding NaOH (20%). Extraction with Et₂O, washing with water, drying over MgSO₄, filtration and evaporation to dryness are carried out. The expected product is obtained in the form an oil.

Preparation 9: 2-(5-Methoxybicyclo[4.2.0]octa-1,3,5-trien-7-yl)methylamine 3 g (19 mmol) of 5-methoxybicyclo[4.2.0]octa-1,3,5-triene-7-carbonitrile in 45 mL of methanol and 45 mL of a 7M ammoniacal methanol solution are hydrogenated in the presence of 1.5 g of Raney nickel 50% in water at atmospheric pressure. After reacting for two hours, the reaction mixture is filtered off and evaporated to yield the expected product.

Preparation 10: 2-(2,3-Dimethoxybicyclo[4.2.0]octa-1,3,5-trien-7-yl)methylamine Obtained in the same manner as the product of Preparation 9 but using 2,3-dimethoxybicyclo[4.2.0]octa-1,3,5-triene-7-carbonitrile.

Preparation 11: 2-(2,3,4-Trimethoxybicyclo[4.2.0]octa-1,3,5-trien-7-yl)methylamine Obtained in the same manner as the product of Preparation 9, but using 2,3,4-trimethoxybicyclo[4.2.0]octa-1,3,5-triene-7-carbonitrile.

Preparation 12: (Cyclopropylmethyl){[(7S)-3,4-dimethoxybicyclo[4.2.0]octa-1,3,5-trien-7-yl]methyl}amine

Step 1: {[(7S)-3,4-Dimethoxybicyclo[4.2.0]octa-1,3,5-trien-7-yl]methyl}cyclopropane-carboxamide To 4.6 g (20 mmol) of {[(7S)-3,4-dimethoxybicyclo[4.2.0]octa-1,3,5-trien-7-yl]methyl}amine hydrochloride in 60 mL of dichloromethane, at ambient temperature, there are added, all at once, 6.1 mL (44 mmol/2.2 eq.) of triethylamine and stirring is carried out for about 30 minutes. There are then added dropwise, over 40 minutes, 2 mL (22 mmol/1.1 eq.) of cyclopropanecarboxylic acid chloride. The mixture is then stirred at ambient temperature for 1 hour 30 minutes and is then transferred to a separating funnel; 60 mL of dichloromethane are added and successive washing with 40 mL of water, two 40 mL quantities of 1N hydrochloric acid, two 40 mL quantities of saturated aqueous sodium hydrogen carbonate solution and 40 mL of water are carried out. After drying over magnesium sulphate, filtration and concentration, the desired product is collected.

Step 2: (Cyclopropylmethyl){[(7S)-3,4-dimethoxybicyclo[4.2.0]octa-1,3,5-trien-7-yl]-methyl}-amine To 1.2 g (30 mmol) of lithium aluminium hydride suspended in 40 mL of THF, at ambient temperature, there is added, dropwise, a solution of 5.2 g (20 mmol) of the preceding compound in 80 mL of THF, followed by heating at reflux for 4 hours 30 minutes. Cooling to about 0° C. is carried out and there are then added, cautiously, in succession, 0.79 mL of water, 0.63 mL of 20% aqueous sodium hydroxide solution and 2.9 mL of water. Stirring at ambient temperature is carried out, and then the salts are filtered off over a frit, rinsing with THF. The combined filtrates are concentrated to yield the desired product.

Preparation 13: {[(7S)-3,4-Dimethoxybicyclo[4.2.0]octa-1,3,5-trien-7-yl]methyl}-ethanamine The procedure is as in Preparation 12, Steps A and B, but using acetyl chloride in Step A instead of cyclopropanecarboxylic acid chloride.

Preparation 14: N-Benzyl-1-[(7S)-3,4-dimethoxybicyclo[4.2.0]octa-1,3,5-trien-7-yl]methanamine The procedure is as in Preparation 12, Steps A and B, but using benzoyl chloride in Step A instead of cyclopropanecarboxylic acid chloride.

Preparation 15: (Cyclopentylmethyl){[(7S)-3,4-dimethoxybicyclo[4.2.0]octa-1,3,5-trien-7-yl]methyl}amine The procedure is as in Preparation 12, Steps A and B, but using cyclopentanecarboxylic acid chloride in Step A instead of cyclopropanecarboxylic acid chloride.

Preparation 16: (Cyclobutylmethyl){[(7S)-3,4-dimethoxybicyclo[4.2.0]octa-1,3,5-trien-7-yl]methyl}amine The procedure is as in Preparation 12, Steps A and B, but using cyclobutanecarboxylic acid chloride in Step A instead of cyclopropanecarboxylic acid chloride.

Preparation 17: N-{[(7S)-3,4-Dimethoxybicyclo[4.2.0]octa-1,3,5-trien-7-yl]-methyl}-2,2,2-trifluoro-ethanamine

Step 1: {N-([(7S)-3, 4-Dimethoxybicyclo[4.2.0]octa-1,3,5-trien-7-yl]-methyl}-2,2,2-trifluoroacetamide To 2.9 g (15 mmol) of {[(7S)-3,4-dimethoxybicyclo[4.2.0]octa-1,3,5-trien-7-yl]methyl}amine in 7.5 mL of methanol, at ambient temperature, there are added, all at once, 2.1 mL (15 mmol/1 eq.) of triethylamine, and then, dropwise, over 20 minutes, 2.3 mL (19 mmol/1.25 eq.) of ethyl trifluoroacetate. Stirring is carried out at ambient temperature for 2 hours, followed by evaporating to dryness. The residue is taken up in 100 mL of dichloromethane, and washing with 50 mL of 1N hydrochloric acid and then 50 mL of water and drying over magnesium sulphate are carried out. After filtration and concentration, the desired product is collected.

Step 2: N-{[(7S)-3,4-Dimethoxybicyclo[4.2.0]octa-1,3,5-trien-7-yl]-methyl}-2,2,2-trifluoroethanamine To 4.07 g (14.0 mmol) of the compound of Step 1 in 28 mL of THF, at about 0° C., there are added dropwise, over 10 minutes, 21 mL (21 mmol/1.5 eq.) of a 1M solution of borane in THF, and then heating at reflux is carried out for 18 hours. The mixture is allowed to cool and 14 mL of a 2.6N ethanolic HCl solution are added dropwise; then the mixture is heated at reflux again for 2 hours. The mixture is allowed to cool, the solid is filtered off over a frit, rinsed with ether and dried in vacuo to obtain the hydrochloride and, after treatment in a basic medium, the expected product.

Preparation 18: N-{[(7S)-3,4-Dimethoxybicyclo[4.2.0]octa-1,3,5-trien-7-yl]-methyl}prop-2-en-1-amine To 3.9 g (20 mmol) of {[(7S)-3,4-dimethoxybicyclo[4.2.0]octa-1,3,5-trien-7-yl]methyl}amine in 40 mL of acetone, at ambient temperature, there are added, all at once, 4.1 g (30 mmol/1.5 eq.) of potassium carbonate, and then there are quickly added dropwise 1.9 mL (22 mmol/1.1 eq.) of allyl bromide. Stirring is carried out at ambient temperature for 60 hours; the salts are then filtered off and the filtrate is concentrated. The residue (4.8 g) is chromatographed over 300 g of silica (eluant: dichloromethane/ethanol/ammonia: 98/2/0.2) to yield the desired product.

Preparation 19: N-{[(7S)-3,4-Dimethoxybicyclo[4.2.0]octa-1,3,5-trien-7-yl]-methyl}cyclopentanamine At ambient temperature, 2.9 g (15 mmol) of {[(7S)-3,4-dimethoxybicyclo[4.2.0]octa-1,3,5-trien-7-yl]methyl}amine and 1.3 mL (15 mmol/1 eq.) of cyclopentanone are mixed into 60 mL of dichloromethane. There are then added 4.8 g (22.5 mmol/1.5 eq.) of sodium triacetoxyborohydride and then 0.86 mL (15 mmol/1 eq.) of acetic acid, and stirring is carried out at ambient temperature for 4 hours. 90 mL of 1N sodium hydroxide solution are then poured in; extraction with two 120 mL quantities of ether is then carried out. The combined organic phases are washed with 90 mL of water and then with 90 mL of saturated aqueous sodium chloride solution and are then dried over magnesium sulphate. After filtration and concentration, the desired product is collected.

Preparation 20: N-{[(7S)-3,4-Dimethoxybicyclo[4.2.0]octa-1,3,5-trien-7-yl]-methyl}cyclobutanamine The procedure is as in Preparation 19, but using cyclobutanone instead of cyclopentanone.

Preparation 21: (7-Aminomethyl)-bicyclo[4.2.0]octa-1,3,5-trien-3-yl trifluoromethylsulphonate Step 1: 7-Cyanobicyclo[4.2.0]octa-1,3,5-trien-3-yl trifluoromethanesulphonate 2.4 mL of triflic anhydride (1.2 equivalents) are poured at 0° C., over 1 hour, into a solution of 2 g (13.8 mmoles) of 3-hydroxy-bicyclo[4.2.0]octa-1,3,5-triene-7-carbonitrile in 40 mL of dichloromethane and 3.9 mL (2 equivalents) of triethylamine. Stirring is carried out for 3 days at 25° C. The reaction mixture is poured into water, extracted with dichloromethane, dried over MgSO$_4$, filtered and evaporated to obtain 3.8 g of an oil. This residue is purified by flash chromatography over 150 g of silica; eluant=100% toluene. The expected product is obtained in the form of an oil.

Step 2: (7-Aminomethyl)-bicyclo[4.2.0]octa-1,3,5-trien-3-yl trifluromethylsulphonate 2.7 g (9.74 mmoles) of the product of Step 1 are dissolved in 40 mL of methanol. 40 mL of a (7N) MeOH—NH$_3$ solution and 1 g of Raney nickel are added. Hydrogenation is carried out under a pressure of 5 bar, at 25° C., for 4 days. Filtration over Celite and evaporation of the filtrate to dryness are carried out. The expected product is obtained in the form of an oil.

Preparation 22: (7-Aminomethyl)bicyclo[4.2.0]octa-1,3,5-trien-3-yl dimethylsulphamate Step 1: 7-Cyanobicyclo[4.2.0]octa-1,3,5-trien-3-yl dimethylsulphamate 2 g (13.8 mmoles) of 3-hydroxy-bicyclo[4.2.0]octa-1,3,5-triene-7-carbonitrile are mixed into 40 mL of dichloromethane, 3.9 g (2 equivalents) of triethylamine and 1.63 mL (1.1 equivalents) of dimethylsulphamoyl chloride. Stirring is carried out at 25° C. for 4 days. The reaction mixture is poured into water, extracted with dichloromethane, dried over MgSO$_4$, filtered and evaporated to obtain an oil. This residue is purified by flash chromatography over 70 g of silica (eluant: dichloromethane/toluene: 50/50). The expected product is obtained in the form of a white solid.

Melting point (M.K.)=78-79° C.

Step 2: (7-Aminomethyl)bicyclo[4.2.0]octa-1,3,5-trien-3-yl dimethylsulphamate 1.8 g (7.1 mmoles) of the product of Step 1 are dissolved in 40 mL of methanol. 40 mL of a (7N) MeOH—NH$_3$ solution and 1 g of Raney nickel are added. Hydrogenation is carried out under a pressure of 5 bar, at 25° C., for 4 days. Filtration over Celite and evaporation of the filtrate to dryness are carried out. There is obtained an oil which is purified by flash chromatography over 50 g of silica (eluant: dichloromethane/ethanol: 90/10). The expected product is obtained in the form an oil.

Preparation 23: (5,6-Dihydrocyclobuta[4,5]benzo[1,2-b]furan-6-yl-methyl)-amine 7 g (41.3 mmoles) of 5,6-dihydrocyclobuta[4,5]benzo[1,2-b]furan-6-carbonitrile are dissolved in 490 mL of ethanol. 70 mL of 28% NH$_4$OH solution and 1 g of Raney nickel are added. Hydrogenation is carried out under a pressure of 5 bar, at 25° C., for 3 days. Filtration over Celite and evaporation of the filtrate to dryness are carried out. The expected product is obtained in the form of a yellow oil.

Preparation 24:
2-(Bromomethyl)-5,6-dimethoxyindan 1 g (4.8 mmoles) of (5,6-dimethoxy-2,3-dihydro-1H-inden-2-yl)methanol is dissolved in 20 mL of dichloromethane and 1 mL of triethylamine. Cooling to 0° C. is carried out and 0.41 mL (1.1 equivalents) of mesyl chloride is poured in. Stirring is carried out at 25° C. for 1 hour. Hydrolysis is carried out using 30 g of ice. Separation is carried out, and washing with HCl (1N) and then with H$_2$O. Drying over MgSO$_4$, filtration and evaporation are carried out. 1.2 g of a beige solid are obtained which is dissolved in 30 mL of acetone. 0.83 g of LiBr (2 equivalents) is added and stirring is carried out at 25° C. for 12 hours. The acetone is evaporated off, the residue is taken up in water and extracted with diethyl ether. The organic phase is separated off, dried over MgSO$_4$, filtered and evaporated. The expected product is obtained in the form of an oil.

Preparation 25: 2-[{[(7S)-3,4-Dimethoxybicyclo[4.2.0]octa-1,3,5-trien-7-yl]methyl}(methyl)amino]ethanol At ambient temperature, 1.04 g (5 mmol) of {[(7S)-3,4-dimethoxybicyclo[4.2.0]octa-1,3,5-trien-7-yl]methyl}methylamine, 0.44 mL (6 mmol/1.2 eq.) of 2-bromoethanol and 2.07 g (15 mmol/3 eq.) of potassium carbonate are mixed into 10 mL of acetonitrile. Refluxing is carried out overnight, followed by drying. The residue is taken up in dichloromethane, washed with water and dried over magnesium sulphate to yield, after concentration, the desired product.

Preparation 26: 2-[{[(7R)-3,4-Dimethoxybicyclo[4.2.0]octa-1,3,5-trien-7-yl]methyl}(methyl)amino]ethanol Obtained as in Preparation 25 but replacing the {[(7S)-3,4-dimethoxybicyclo[4.2.0]octa-1,3,5-trien-7-yl]methyl}methylamine by {[(7R)-3,4-dimethoxybicyclo[4.2.0]octa-1,3,5-trien-7-yl]methyl}methylamine.

Preparation 27: N-{[(7S)-3,4-Dimethoxybicyclo[4.2.0]octa-1,3,5-trien-7-yl]methyl}-N-methyl-ethane-1,2-diamine Step 1: [{[(7S)-3, 4-Dimethoxybicyclo[4.2.0]octa-1,3,5-trien-7-yl]methyl}(methyl)amino]acetonitrile.

At ambient temperature, 1.04 g (5 mmol) of {[(7S)-3,4-dimethoxybicyclo[4.2.0]octa-1,3,5-trien-7-yl]methyl}methylamine, 0.35 mL (5 mmol/1 eq.) of bromoacetonitrile and 2.16 g (20 mmol/4 eq.) of sodium carbonate are mixed into 16 mL of methyl isobutyl ketone. Refluxing is carried out overnight, followed by drying. The residue is taken up in water and the aqueous phase is extracted with dichloromethane. The combined organic phases are dried over magnesium sulphate to yield, after concentration, the expected product.

Step 2: N-{[(7S)-3, 4-Dimethoxybicyclo[4.2.0]octa-1,3,5-trien-7-yl]methyl}-N-methyl-ethane-1,2-diamine A solution of 1.1 g (4.5 mmol) of the compound of Step 1 in 10 mL of THF is poured dropwise into 0.21 g (5.4 mmol) lithium aluminium hydride suspended in 5 mL of THF, at ambient temperature, and is then stirred at ambient temperature for 5 hours. Cooling to about 0° C. is carried out and there are then added, cautiously, in succession, 0.14 mL of water, 0.11 mL of 20% aqueous sodium hydroxide solution and 0.51 mL of water. Stirring is carried out overnight at ambient temperature, and then the salts are filtered off over a frit and rinsed with THF. The combined filtrates are concentrated to yield the desired product.

Preparation 28: N-{[(7R)-3,4-dimethoxybicyclo[4.2.0]octa-1,3,5-trien-7-yl]methyl}-N-methyl-ethane-1,2-diamine Obtained as in Preparation 27 but replacing the {[(7S)-3,4-dimethoxybicyclo[4.2.0]octa-1,3,5-trien-7-yl]methyl}methylamine by {[(7R)-3,4-dimethoxybicyclo[4.2.0]octa-1,3,5-trien-7-yl]methyl}methylamine.

Preparation 29: [(4-Methoxy-3-methyl-bicyclo[4.2.0]octa-1,3,5-trien-7-yl)methyl]amine Step 1:
3-(3-Bromo-4-methoxy-5-methylphenyl)propanenitrile 62.8 g (358.4 mmol) of 3-(4-methoxy-5-methylphenyl)propanenitrile are dissolved in 390 mL of acetic acid. There are then added, all at once, 58.8 g (716.8 mmol/2 eq.) of sodium acetate and then, dropwise, 20.2 mL (394.2 mmol/1.1 eq.) of bromine, and stirring is carried out at ambient temperature overnight. The reaction mixture is then poured into 2 liters of water, and the aqueous phase is extracted 3 times with 500 mL of dichloromethane. The combined organic phases are washed successively with 500 mL of water, 500 mL of saturated aqueous sodium hydrogen carbonate solution and 500 mL of water, and are dried over magnesium sulphate. After concentration, the expected product is collected.

Step 2: 4-Methoxy-3-methylbicyclo[4.2.0]octa-1,3,5-triene-7-carbonitrile 94 g (370 mmol) of the preceding compound dissolved in 230 mL of ether are poured into sodium amide (925 mmol/2.5 eq.) in 1850 mL of liquid ammonia. After stirring for 3 hours at reflux of the ammonia, the reaction is stopped by adding 99 g (5 eq.) of solid ammonium chloride, and the ammonia is then allowed to evaporate. The residue is taken up in 500 mL of water and 500 mL of dichloromethane, stirring is carried, the phases are separated, and the aqueous phase is extracted again twice with 500 mL of dichloromethane. The combined organic phases are dried over magnesium sulphate and concentrated. The residue (68 g) is chromatographed over 800 g of silica (eluant: dichloromethane/cyclohexane: 50/50) to yield, after recrystallisation from 150 mL of isopropyl ether, the desired product.

Step 3: [(4-Methoxy-3-methyl-bicyclo[4.2.0]octa-1,3,5-trien-7-yl)methyl]amine

To 4.0 g (23.1 mmol) of the preceding compound dissolved in 75 mL of methanol and 75 mL of 7N ammoniacal methanol there are added 3.3 mL of Raney nickel. Hydrogenation is carried out at ambient temperature and ordinary pressure for 2 hours. Filtration over Celite, rinsing with methanol and concentration are carried out to obtain the desired product.

Preparation 30: [(3-Methoxy-4-methyl-bicyclo[4.2.0]octa-1,3,5-trien-7-yl)-methyl]amine Step 1: 5-Methoxy-4-methylbenzaldehyde At ambient temperature, 36.35 g (238.8 mmol) of (3-methoxy-4-methylphenyl)-methanol and 207.6 g (2.4 moles/10 eq.) of manganese oxide are mixed into 730 mL of dichloromethane. Stirring is carried out at ambient temperature overnight, followed by filtration over Celite and rinsing with dichloromethane. After concentration of the combined filtrates, the desired product is obtained.

Step 2: 2-Bromo-5-methoxy-4-methylbenzaldehyde

At ambient temperature, 35.5 g (238.7 mmol) of the preceding compound are dissolved in 290 mL of dichloromethane, 29.4 g (358 mmol/1.5 eq.) of sodium acetate are added all at once and then a solution of 15 mL (286.4 mmol/1.2 eq.) of bromine in 130 mL of dichloromethane is poured in dropwise. Stirring is carried out at ambient temperature for 4 hours and the insoluble material is filtered off; the filtrate is washed with 1N sodium thiosulphate solution and dried over magnesium sulphate. After concentration, the residue is recrystallised from 130 mL of heptane to yield the desired product.

Step 3: 3-(2-Bromo-5-methoxy-4-methylphenyl)acrylonitrile 4.22 g (183.6 mmol/1 eq.) of sodium are dissolved in 180 mL of anhydrous ethanol and the solution is brought to about 0° C. There are then added dropwise 29.7 mL (183.6 mmol/1 eq.) of diethoxyphosphonoacetonitrile. Stirring is carried out at 0° C. for 30 minutes; 42.05 g (183.6 mmol) of the preceding compound are added in portions and then stirring is carried out again at 0° C. for 30 minutes and then at ambient temperature for 1 hour. The reaction mixture is poured into 1800 mL of water and stirring is carried out for 30 minutes; the solid material is then filtered off, washed with water and dried in vacuo to obtain the desired product.

Step 4: 3-(2-Bromo-5-methoxy-4-methylphenyl)propanenitrile

At ambient temperature, 46 g (182.5 mmol) of the preceding compound and 27.7 g (730 mmol/4 eq.) of sodium borohydride are mixed into 380 mL of isopropanol, and then heating at reflux is carried out for 2 days (1 eq. of sodium borohydride is added after 1 day). The mixture is allowed to cool and then concentrated. The residue is taken up in 630 mL of a mixture of water and ice and is then acidified to pH 1 by cautiously adding 90 mL of concentrated hydrochloric acid. This aqueous phase is extracted twice with ethyl acetate. The combined organic phases are washed with saturated aqueous sodium chloride solution and then dried over magnesium sulphate. After concentration, the residue is recrystallised from 100 mL of heptane to yield the desired product.

Step 5: 3-Methoxy-4-methylbicyclo[4.2.0]octa-1,3,5-triene-7-carbonitrile

The procedure as in Step 2 of Preparation 29 is carried out to yield the expected product.

Step 6: [(3-Methoxy-4-methyl-bicyclo[4.2.0]octa-1,3,5-trien-7-yl)methyl]amine

The procedure as in Step 3 of Preparation 29 is carried out to yield the expected product.

EXAMPLE 1

N-[(3,4-Dimethoxybicyclo[4.2.0]octa-1,3,5-trien-7-yl)methyl]-3-(7,8-dimethoxy-1,2,4,5-tetrahydro-3H-3-benzazepin-3-yl)-N-methyl-3-oxopropan-1-amine hydrochloride Step 1: 7,8-Dimethoxy-1,3,4,5-tetrahydro-2H-3-benzazepin-2-one At ambient temperature, 35 g (159.6 mmol) of 7,8-dimethoxy-1,3-dihydro-2H-3-benzazepin-2-one are dissolved in a mixture of 525 mL of ethanol and 175 mL of ethyl acetate. There are then added 7 g (20% by weight) of palladium-on-carbon 10% and hydrogenation is carried out at 65° C. and 3.5 bars for 22 hours. The catalyst is filtered off over Celite; rinsing with a mixture of ethanol/ethyl acetate and evaporation to dryness are carried out to yield the desired product.

Step 2: 7,8-Dimethoxy-2,3,4,5-tetrahydro-1H-3-benzazepine hydrochloride 22.13 g (100 mmol) of the product obtained in Step 1, suspended in 250 mL of THF, are cooled to 0° C. There are then added, dropwise, over 15 minutes, 250 mL of borane/THF (1M in the THF) and heating is carried out at 80° C. for 24 hours. Cooling is carried out and there are then added, dropwise, 250 mL of ethanol, and then 2.6N ethanolic HCl. Heating at reflux is carried out for 40 minutes; some light insoluble material is filtered off and evaporation to dryness is carried out. The residue thereby obtained is recrystallised from a mixture of 150 mL of isopropanol and 20 mL of water to yield the desired product.

Step 3: 3-Acryloyl-7,8-dimethoxy-2,3,4,5-tetrahydro-1H-3-benzazepine

At ambient temperature, 70 g (287.2 mmol) of the product obtained in Step 2 are dissolved in 1200 mL of dichloromethane, and then 100 mL (718 mmol/2.5 eq.) of triethylamine are added all at once. The mixture is brought to 0° C. and a solution of 25.8 mL (315.9 mmol/1.1 eq.) of acryloyl chloride in 270 mL of dichloromethane is poured in dropwise, maintaining the temperature at about 0° C. After 2 hours at 0° C., the mixture is stirred at ambient temperature overnight. Washing with 750 mL of water, 750 mL of 1N hydrochloric acid and 750 mL of water and then drying over magnesium sulphate are then carried out. After filtration and evaporation, the residue is chromatographed over 3.2 kg of silica (eluant: dichloromethane/ethanol: 95/5), followed by recrystallisation from isopropanol. After filtration over a frit and drying in vacuo at 50° C., the desired product is obtained.

Step 4: N-[(3,4-Dimethoxybicyclo[4.2.0]octa-1,3,5-trien-7-yl)methyl]-3-(7,8-dimethoxy-1,2,4,5-tetrahydro-3H-3-benzazepin-3-yl)-N-methyl-3-oxopropan-1amine hydrochloride 1.05 g (4.0 mmol) of the product obtained in Step 3 and 0.82 g (4.0 mmol) of {[(7R,S)-3,4-dimethoxybicyclo[4.2.0]octa-1,3,5-trien-7-yl]methyl}methylamine are dissolved in 5 mL of THF. Heating at reflux (oil bath at 90° C.) is carried out overnight under a current of nitrogen so that the solvent is gradually evaporated off. The residue obtained is chromatographed immediately over silica (eluant: dichloromethane/ethanol/ammonia: 95/5/0.5). After dissolving in isopropanol, treatment with 1.1 eq. of ethereal HCl is carried out and stirring is continued until precipitation occurs. After drying, the solid obtained is made more solid in a mixture of ethyl acetate (10 mL) and acetonitrile (20 mL) to yield, after filtration and drying, the expected product.
Melting point (M.K.): 176-179° C.

EXAMPLE 2

N-{[(7R)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-N-methyl-3-oxopropan-1-amine hydrochloride Obtained in the same manner as the product of Example 1, but with replacement of the racemic [(3,4-dimethoxybicyclo[4.2.0]octa-1,3,5-trien-7-yl)methyl]methylamine in Step 4 by {[(7R)-3,4-dimethoxybicyclo[4.2.0]octa-1,3,5-trien-7-yl]methyl}methylamine.
Melting point (M.K.): 155-158° C.
Optical rotation: solvent: DMSO, C=0.01 g/cm$^3$, T=20° C., L=589 nm, $\alpha_D$=−1.46.

EXAMPLE 3a

N-{[(7S)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-N-methyl-3-oxopropan-1-amine hydrochloride Obtained in the same manner as the product of Example 1, but with replacement of the racemic [(3,4-dimethoxybicyclo[4.2.0]octa-1,3,5-trien-7-yl)methyl]methylamine in Step 4 by {[(7S)-3,4-dimethoxybicyclo[4.2.0]octa-1,3,5-trien-7-yl]methyl}methylamine.
Melting point (M.K.): 157-160° C.
Optical rotation: solvent: DMSO, C=0.01 g/cm$^3$, T=20° C., L=589 nm, $\alpha_D$=+1.6.
IR (cm$^{-1}$): 2438 (NH$^+$), 1625 (C=O), 1234-1203-1179 (C—O—C), 865-846 (CH—Ar).

EXAMPLE 3b

N-{[(7S)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-N-methyl-3-oxopropan-1-amine fumarate The expected product is obtained by converting N-{[(7S)-3,4-dimethoxybicyclo[4.2.0]octa-1,3,5trien-7-yl]methyl}-3 (7,8-dimethoxy-1,2,4,5-tetrahydro-3H-3-benzazepin-3-yl)-N-methyl-3-oxopropan-1-amine, obtained by returning the hydrochloride obtained in Example 3a to the base, to a salt using fumaric acid.
Elemental Microanalysis:

|  | % C | % H | % N |
| --- | --- | --- | --- |
| Calculated | 63.68 | 6.90 | 4.79 |
| Found | 63.40 | 6.88 | 4.90 |

EXAMPLE 3c

N-{[(7S)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-N-methyl-3-oxopropan-1-amine hemipamoate The expected product is obtained by converting N-{[(7S)-3,4-dimethoxybicyclo[4.2.0]octa-1,3,5-trien-7-yl]methyl}-3 (7,8-dimethoxy-1,2,4,5-tetrahydro-3H-3-benzazepin-3-yl)-N-methyl-3-oxopropan-1-amine, obtained by returning the hydrochloride obtained in Example 3a to the base, to a salt using pamoic acid.
Elemental Microanalysis:

|  | % C | % H | % N |
| --- | --- | --- | --- |
| Calculated | 69.77 | 6.69 | 4.23 |
| Found | 69.38 | 6.56 | 3.91 |

EXAMPLE 3d

N-{[(7S)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-N-methyl-3-oxopropan-1-amine heminapadisylate The expected product is obtained by converting N-{[(7S)-3,4-dimethoxybicyclo[4.2.0]octa-1,3,5-trien-7-yl]methyl}-3 (7,8-dimethoxy-1,2,4,5-tetrahydro-3H-3-benzazepin-3-yl)-N-methyl-3-oxopropan-1-amine, obtained by returning the hydrochloride obtained in Example 3a to the base, to a salt using 1,5-naphthalenedisulphonic acid.
NMR $^1$H:

| (aa) | δ = 10.77 ppm (1H; bs) |
| --- | --- |
| (a) | δ = 6.74 ppm (1H; s) |
| (b) | δ = 6.70 ppm (1H; s) |
| (c) | δ = 6.68 ppm (1H; s) |
| (d) | δ = 6.65 ppm (1H; s) |
| (e) | δ = 3.874 ppm (3H; s) |
| (f) | δ = 3.871 ppm (3H; s) |
| (g) | δ = 3.858 ppm (3H; s) |
| (h) | δ = 3.851 ppm (3H; s) |
| (i) | δ = 3.73 ppm (2H; m) |
| (j) | δ = 3.60 ppm (2H; m) |
| (k) | δ = 3.59 ppm (1H; m) |
| (l, l') | δ = 3.29 and 2.77 ppm (2H; dd) $J_{ll'}$ = 13.4 Hz; $J_{lk}$ = 4.7 Hz; $J_{l'k}$ = 1.9 Hz |
| (m) | δ = 2.87 ppm (2H; m) |
| (n) | δ = 2.86 ppm (2H; m) |
| (o) | δ = 2.85 ppm (2H; m) |
| (p) | δ = 2.81 ppm (1H; dd) $J_{pp'}$ = 12.5 Hz; $J_{pk}$ = 5.9 Hz |
| (p') | δ = 2.63 ppm (1H; m) |
| (q) | δ = 2.65 ppm (2H; m) |
| (r) | δ = 2.40 ppm (3H; s) |
| (x) | δ = 2.40 ppm (1H; d) $J_{xz}$ = 8.7 Hz |
| (y) | δ = 2.40 ppm (1H; d) $J_{yz}$ = 7.2 Hz |
| (z) | δ = 2.40 ppm (1H; dd) |

EXAMPLE 4

N-{[(7S)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine hydrochloride Obtained in the same manner as the product of Example 1, but with replacement of the racemic [(3,4-dimethoxybicyclo[4.2.0]octa-1,3,5-trien-7-yl)methyl]methylamine in Step 4 by {[(7S)-3,4-dimethoxybicyclo[4.2.0]octa-1,3,5-trien-7-yl]methyl}amine and of the THF by dioxane.
Melting point (M.K.): 177-180° C.
Optical rotation: solvent: MeOH, C=0.01 1 g/cm$^3$, T=20° C., L=589 nm, $\alpha_D$=−4.15.
IR (cm$^{-1}$): 2723 (NH), 1645 (C═O).

EXAMPLE 5

N-[(4,5-Dimethoxybicyclo[4.2.0]octa-1,3,5-trien-7-yl)methyl]-3-(7,8-dimethoxy-1,2,4,5-tetrahydro-3H-3-benzazepin-3-yl)-3-oxopropan-1-amine hydrochloride Obtained in the same manner as the product of Example 1, but with replacement of the [(3,4-dimethoxybicyclo[4.2.0]octa-1,3,5-trien-7-yl)methyl]methylamine in Step 4 by the product of Preparation 1 and of the THF by dioxane.
Melting point(M.K.): 199-201° C.
IR (cm$^{-1}$): 1645 (C═O), 3000 to 2400 (NH$_2^+$).

EXAMPLE 6

N-[2-(5,6-Dimethoxy-2,3-dihydro-1H-inden-2-yl)ethyl]-3-(7,8-dimethoxy-1,2,4,5-tetrahydro-3H-3-benzazepin-3-yl)-N-methyl-3-oxopropan-1-amine hydrochloride Obtained in the same manner as the product of Example 1, but with replacement of the [(3,4-dimethoxybicyclo[4.2.0]octa-1,3,5-trien-7-yl)methyl]methylamine in Step 4 by [2-(5,6-dimethoxy-2,3-dihydro-1H-inden-2-yl)ethyl]methylamine.
Melting point (M.K.)=193-199° C.

EXAMPLE 7

N-[(5,6-Dimethoxy-2,3-dihydro-1H-inden-2-yl)methyl]-3-(7,8-dimethoxy-1,2,4,5-tetrahydro-3H-3-benzazepin-3-yl)-N-methyl-3-oxopropan-1-amine hydrochloride Obtained in the same manner as the product of Example 1, but with replacement of the [(3,4-dimethoxybicyclo[4.2.0]octa-1,3,5-trien-7-yl)methyl]methylamine in Step 4 by [(5,6-dimethoxy-2,3-dihydro-1H-inden-2-yl)methyl]methylamine.
Melting point (M.K.)=194-197° C.

EXAMPLE 8

N-[(2,3-Dimethoxybicyclo[4.2.0]octa-1,3,5-trien-7-yl)methyl]-3-(7,8-dimethoxy-1,2,4,5-tetrahydro-3H-3-benzazepin-3-yl)-3-oxopropan-1-amine hydrochloride Obtained in the same manner as the product of Example 1, but with replacement of the [(3,4-dimethoxybicyclo[4.2.0]octa-1,3,5-trien-7-yl)methyl]methylamine in Step 4 by the product of Preparation 10.
Melting point (M.K.)=220-222° C.

EXAMPLE 9

N-[(2,3,4-Trimethoxybicyclo[4.2.0]octa-1,3,5-trien-7-yl)methyl]-3-(7,8-dimethoxy-1,2,4,5-tetrahydro-3H-3-benzazepin-3-yl)-3-oxopropan-1-amine hemifumarate Obtained in the same manner as the product of Example 1, but with replacement of the [(3,4-dimethoxybicyclo[4.2.0]octa-1,3,5-trien-7-yl)methyl]methylamine in Step 4 by the product of Preparation 11. Conversion to a salt is carried out in the presence of fumaric acid.
Melting point (M.K.)=155-157° C.

EXAMPLE 10

3-(7,8-Dimethoxy-1,2,4,5-tetrahydro-3H-3-benzazepin-3-yl)-N-[(5-methoxybicyclo[4.2.0]octa-1,3,5-trien-7-yl)methyl]-3-oxopropan-1-amine hydrochloride Obtained in the same manner as the product of Example 1, but with replacement of the [(3,4-dimethoxybicyclo[4.2.0]octa-1,3,5-trien-7-yl)methyl]methylamine in Step 4 by the product of Preparation 9 and of the THF by dioxane.
Melting point (M.K.)=185-187° C.

EXAMPLE 11

N-{[(7S)-3,4-Dimethoxybicyclo[4.2.0]octa-1,3,5-trien-7-yl]methyl}-3-(7-methoxy-1,2,4,5-tetrahydro-3H-3-benzazepin-3-yl)-3-oxopropan-1-amine hydrochloride Obtained in the same manner as the product of Example 1, but with replacement, in Step 1, of the 7,8-dimethoxy-1,3-dihydro-2H-3-benzazepin-2-one by 8-methoxy-1,3-dihydro-2H-3-benzazepin-2-one and, in Step 4, of the racemic (3,4-dimethoxybicyclo[4.2.0]octa-1,3,5-trien-7-yl)methyl]methylamine by {[(7S)-3,4-dimethoxybicyclo[4.2.0]octa-1,3,5-trien-7-yl]methyl}amine and of the THF by dioxane.
Melting point (M.K.)=171-173° C.
IR (cm$^{-1}$): 1636 (C═O), 3000 to 2400 (NH$_2^+$).

EXAMPLE 12

N-[2-(5,6-Dimethoxy-2,3-dihydro-1H-inden-2-yl)methyl]-3-(7,8-dimethoxy-1,2,4,5-tetrahydro-3H-3-benzazepin-3-yl)-3-oxopropan-1-amine hydrochloride Step 1: N-Benzyl-3-(7,8-dimethoxy-1,2,4,5-tetrahydro-3H-3-benzazepin-3-yl)-3-oxopropan-1amine The procedure is as in Step 4 of Example 1, but with replacement of the [(3,4-dimethoxy-bicyclo[4.2.0]octa-1,3,5-trien-7-yl)methyl]methylamine by benzylamine.
Melting point (M.K.)=100-102° C.

Step 2: N-Benzyl-N-[(5,6-dimethoxy-2,3-dihydro-1H-inden-2-yl)methyl]-3-(7,8-dimethoxy-1,2,4,5-tetrahydro-3H-3-benzazepin-3-yl)-3-oxopropan-1-amine 1.7 g (4.6 mmoles) of the product of Step 1 and 1.25 g (1 equivalent) of the product of Preparation 24 are dissolved in 20 mL of acetonitrile. 5.1 g (8 equivalents) of $K_2CO_3$ are added and heating at reflux is carried out for 24 hours. The mixture is cooled and filtered and the filtrate is evaporated. A residue is obtained which is purified by chromatography over silica (eluant: $CH_2Cl_2$/ethanol: 95/5) to yield the expected product in the form of an oil.

Step 3: N-[2-(5,6-Dimethoxy-2,3-dihydro-1H-inden-2-yl)methyl]-3-(7,8-dimethoxy-1,2,4,5-tetrahydro-3H-3-benzazepin-3-yl)-3-oxopropan-1-amine hydrochloride 2.3 g (4.1 mmoles) of the product obtained in Step 2 are dissolved in 46 mL of ethanol. 230 mg of Pd/C 5% are added, and hydrogenation is carried out under a pressure of 1 bar and at ambient temperature for 24 hours. The mixture is filtered over Celite, rinsing with ethanol, and the filtrate is evaporated to dryness. 1.95 g of a residue are obtained which is dissolved in 15 mL of ethanol. 2.5 mL of (2M) $Et_2O$—HCl solution are added. A product crystallises out which is filtered off and dried. The expected product is obtained in the form of a white solid.
Melting point (M.K.)=198-204° C.

EXAMPLE 13

3-(7,8-Dimethoxy-1,2,4,5-tetrahydro-3H-3-benzazepin-3-yl)-N-[(2-methoxybicyclo[4.2.0]octa-1,3,5-trien-7-yl)methyl]-3-oxopropan-1-amine hydrochloride At ambient temperature, 0.93 g (3.6 mmol/1 eq.) of the product of Step 3 of Example 1, 0.58 g (3.6 mmol) of the product of Preparation 2 and 0.11 g (0.18 mmol/0.05 eq.) of ytterbium triflate are mixed into 10 mL of toluene. Heating is carried out at 100° C. until the end of the reaction (assessed by TLC) and then evaporation to dryness is carried out. The residue obtained is chromatographed immediately over silica (eluant: dichloromethane/ethanol/ammonia: 95/5/0.5) to yield the expected product in the form of the base. After dissolving in 10 mL of acetonitrile, treatment with 0.56 mL (1.1 eq.) of 3.5N ethanolic HCl is carried out to obtain, after filtration and drying, the expected product.
Melting point (M.K.): 202-204° C.
IR ($cm^{-1}$): 1641 (C=O), 3000 to 2500 ($NH_2^+$).

EXAMPLE 14

3-(7,8-Dimethoxy-1,2,4,5-tetrahydro-3H-3-benzazepin-3-yl)-N-[(3-ethoxybicyclo[4.2.0]octa-1,3,5-trien-7-yl)methyl]-3-oxopropan-1-amine hydrochloride Obtained in the same manner as the product of Example 13, but with replacement of the product of Preparation 2 by that of Preparation 5.
Melting point (M.K.): 221-225° C.

EXAMPLE 15

N-[(3-tert-Butoxybicyclo[4.2.0]octa-1,3,5-trien-7-yl)methyl]-3-(7,8-dimethoxy-1,2,4,5-tetrahydro-3H-3-benzazepin-3-yl)-3-oxopropan-1-amine hemifumarate Obtained in the same manner as the product of Example 13, but with replacement of the product of Preparation 2 by that of Preparation 6 and using fumaric acid instead of hydrochloric acid as salt-forming agent.
Melting point (M.K.)=189-191° C.

EXAMPLE 16

N-(5,6-Dihydrocyclobuta[f][1,3]benzodioxol-5-ylmethyl)-3-(7,8-dimethoxy-1,2,4,5-tetrahydro-3H-3-benzazepin-3-yl)-N-methyl-3-oxopropan-1-amine hydrochloride Obtained in the same manner as the product of Example 13, but with replacement of the product of Preparation 2 by that of Preparation 7.
Melting Point=180-184° C.

EXAMPLE 17

N-(5,6-Dihydrocyclobuta[f][1,3]benzodioxol-5-ylmethyl)-3-(7,8-dimethoxy-1,2,4,5-tetrahydro-3H-3-benzazepin-3-yl)-3-oxopropan-1-amine hydrochloride Obtained in the same manner as the product of Example 13, but with replacement of the product of Preparation 2 by (5,6-dihydrocyclobuta[4,5]benzo[1,2-d][1,3]dioxol-5-ylmethyl)amine.
Melting point (M.K.)=201-207° C.

EXAMPLE 18

N-[2-(5,6-Dimethoxy-2,3-dihydro-1H-inden-2-yl)ethyl]-3-(7,8-dimethoxy-1,2,4,5-tetrahydro-3H-3-benzazepin-3-yl)-3-oxopropan-1-amine hydrochloride Obtained in the same manner as the product of Example 13, but with replacement of the product of Preparation 2 by that of Preparation 8.
Melting point (M.K.)=186-189° C.

EXAMPLE 19

7-({[3-(7,8-Dimethoxy-1,2,4,5-tetrahydro-3H-3-benzazepin-3-yl)-3-oxopropyl]amino}methyl)bicyclo[4.2.0]octa-1,3,5-trien-3-yl trifluoromethanesulphonate hydrochloride Obtained in the same manner as the product of Example 13, but with replacement of the product of Preparation 2 by that of Preparation 21.
Melting point (M.K.): 162-168° C.

EXAMPLE 20

7-({[3-(7,8-Dimethoxy-1,2,4,5-tetrahydro-3H-3-benzazepin-3-yl)-3-oxopropyl]amino}methyl)bicyclo[4.2.0]octa-1,3,5-trien-3-yl dimethylsulphamate hydrochloride Obtained in the same manner as the product of Example 13, but with replacement of the product of Preparation 2 by that of Preparation 22.
Melting point (M.K.): 228-235° C.

EXAMPLE 21

N-(5,6-Dihydrocyclobuta[f][1]benzofuran-6-ylmethyl)-3-(7,8-dimethoxy-1,2,4,5-tetrahydro-3H-3-benzazepin-3-yl)-3-oxopropan-1-amine hydrochloride Obtained in the same manner as the product of Example 13, but with replacement of the product of Preparation 2 by that of Preparation 23.

Melting point (M.K.): 245-255° C.

EXAMPLE 22

N-(Cyclopropylmethyl)-N-{[(7S)-3,4-dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine hydrochloride Obtained in the same manner as the product of Example 13, but with replacement of the product of Preparation 2 by the product of Preparation 12 and of the toluene by dioxane.

Melting point (M.K.)=88-92° C.

Optical rotation: solvent: MeOH, C=0.01 g/cm³, T=20° C., L=589 nm, $\alpha_D$=−13.25

IR (cm⁻¹): 1632 (C=O), 3420 (H$_2$O), 3000 to 2200 (NH⁺).

EXAMPLE 23

N-Allyl-N-{[(7S)-3,4-dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine hydrochloride Obtained in the same manner as the product of Example 13, but with replacement of the product of Preparation 2 by the product of Preparation 18 and of the toluene by dioxane.

Melting point (M.K.)=74-80° C.

Optical rotation: solvent: MeOH, C=0.01 g/cm³, T=20° C., L=589 nm, $\alpha_D$=−4.6

IR (cm⁻¹): 1631 (C=O), 3400 (H$_2$O), 3000 to 2000 (NH⁺).

EXAMPLE 24

N-{[(7S)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-N-ethyl-3-oxopropan-1-amine hemifumarate Obtained in the same manner as the product of Example 13, but with replacement of the product of Preparation 2 by the product of Preparation 13 and of the toluene by dioxane. The salt is formed using fumaric acid.

Melting point (M.K.)=71-73° C.

Optical rotation: solvent: MeOH, C=0.01 g/cm³, T=20° C., L=589 nm, $\alpha_D$=−6.67

IR (cm⁻¹): 2200 to 2700 (NH/OH), 1701-1631 (C=O), 1276-1203 (C—O—C).

EXAMPLE 25

N-{[(7S)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-N-(2,2,2-trifluoroethyl)-3-oxopropan-1-amine hydrochloride Obtained in the same manner as the product of Example 13, but with replacement of the product of Preparation 2 by the product of Preparation 17 and of the toluene by dioxane.

Melting point (M.K.)=68-70° C.

Optical rotation: solvent: MeOH, C=0.01 g/cm³, T=20° C., L=589 nm, $\alpha_D$=−8.04

IR (cm⁻¹): 1633 (C=O), 2800 to 1900 (—NH⁺), 1107 to 1206 (—CF$_3$).

EXAMPLE 26

N-Benzyl-N-{[(7S)-3,4-dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine fumarate Obtained in the same manner as the product of Example 13, but with replacement of the product of Preparation 2 by the product of Preparation 14 and of the toluene by dioxane. The salt is formed using fumaric acid.

Melting point (M.K.): 146-148° C.

Optical rotation: solvent: MeOH, C=0.011 g/cm³, T=20° C., L=589 nm, $\alpha_D$=+2.07

IR (cm⁻¹): 1708 and 1646 (C=O), 3000 to 2500 (—OH).

EXAMPLE 27

N-Cyclopentyl-N-{[(7S)-3,4-dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine fumarate Obtained in the same manner as the product of Example 13, but with replacement of the product of Preparation 2 by the product of Preparation 19 and of the toluene by dioxane.

Melting point (M.K.): 79-82° C.

Optical rotation: solvent: MeOH, C=0.01 g/cm³, T=20° C., L=589 nm, $\alpha_D$=−10.54

IR (cm⁻¹): 1701 and 1635 (C=O), 3000 to 2500 (—OH).

EXAMPLE 28

N-(Cyclopentylmethyl)-N-{[(7S)-3,4-dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine hydrochloride Obtained in the same manner as the product of Example 13, but with replacement of the product of Preparation 2 by the product of Preparation 15 and of the toluene by dioxane.

Melting point (M.K.): 87-90° C.

Optical rotation: solvent: MeOH, C=0.008 g/cm³, T=20° C., L=589 nm, $\alpha_D$=−19.07

IR (cm⁻¹): 2454 (—NH⁺), 1633 (C=O), 1279-1205 (C—O—C).

EXAMPLE 29

N-(Cyclobutylmethyl)-N-{[(7S)-3,4-dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine fumarate Obtained in the same manner as the product of Example 13, but with replacement of the product of Preparation 2 by the product of Preparation 16 and of the toluene by dioxane. Salt formation is carried out in the presence of fumaric acid.
Melting point (M.K.): 68-71° C.
Optical rotation: solvent: MeOH, C=0.01 g/cm$^3$, T=20° C., L=589 nm, $\alpha_D$=−12.04
IR (cm$^{-1}$): 1703 and 1634 (C=O), 1279-1072 (C—O—C).

EXAMPLE 30

N-Cyclobutyl-N-{[(7S)-3,4-dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine hydrochloride At ambient temperature, 1 g (2.2 mmol) of N-{[(7S)-3,4-dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine (obtained by returning the compound of Example 4 to the free base) and 0.17 mL (2.2 mmol/1 eq.) of cyclobutanone are mixed into 7 ml of dichloromethane. Then 0.7 g (3.3 mmol/1.5 eq.) of sodium triacetoxyborohydride and then 0.13 mL (2.2 mmol/1 eq.) of acetic acid are then added, and stirring is carried out at ambient temperature for 5 hours. If the reaction is not complete, there are further added 0.08 mL (0.5 eq.) of cyclobutanone and 350 mg (0.75 eq.) of sodium triacetoxyborohydride and stirring is carried out at ambient temperature for 1 hour 45 minutes more. There are then added of 1N aqueous sodium hydroxide solution and extraction is then carried out twice with 15 mL of ether. The combined organic phases are washed with 10 mL of water and then with 10 mL of saturated aqueous sodium chloride solution and are then dried over magnesium sulphate. After filtration and concentration, the residue (1 g) is chromatographed over a column of 50 g of silica (eluant: dichloromethane/ethanol/ammonia: 98/2/0.2) to yield the desired product in the form of the base. The latter is dissolved in 9 mL of ethyl acetate and 12 mL of ether and converted into a salt using 0.63 mL of 2N ethereal HCl to yield the expected product.
Melting point (M.K.): 93-95° C.
Optical rotation: solvent: MeOH, C=0.01 g/cm$^3$, T=20° C., L=589 nm, $\alpha_D$=−5.63
IR (cm$^{-1}$): 2424 (—NH$^+$), 1633 (C=O), 1205-1107 (C—O—C).

EXAMPLE 31

N-{[(7R)-3,4-Dimethoxybicyclo[4.2.0]octa-1,3,5-trien-7-yl]methyl}-N-methyl-3-(6,7,8-trimethoxy-1,2,4,5-tetrahydro-3H-3-benzazepin-3-yl)-3-oxopropan-1-amine hydrochloride Obtained in the same manner as the product of Example 13, but with replacement of the product of Step 3 of Example 1 by 3-acryloyl-6,7,8-trimethoxy-2,3,4,5-tetrahydro-1H-3-benzazepine, and of the product of Preparation 2 by {[(7R)-3,4-dimethoxybicyclo[4.2.0]octa-1,3,5-trien-7-yl]methyl}methylamine, and of the toluene by THF.
Melting point (M.K.): 83-86° C.

EXAMPLE 32

N-{[(7S)-3,4-Dimethoxybicyclo[4.2.0]octa-1,3,5-trien-7-yl]methyl}-N-methyl-3-(6,7,8-trimethoxy-1,2,4,5-tetrahydro-3H-3-benzazepin-3-yl)-3-oxopropan-1-amine hydrochloride Obtained in the same manner as the product of Example 13, but with replacement of the product of Step 3 of Example 1 by 3-acryloyl-6,7,8-trimethoxy-2,3,4,5-tetrahydro-1H-3-benzazepine, and of the product of Preparation 2 by {[(7S)-3,4-dimethoxybicyclo[4.2.0]octa-1,3,5-trien-7-yl]methyl}methylamine, and of the toluene by THF.
Melting point (M.K.): 83-87° C.
Optical rotation: solvent: MeOH, C=0.01 g/cm$^3$, T=20° C., L=589 nm, $\alpha_D$=−3.00
IR (cm$^{-1}$): 1633 (C=O), 3100 to 2000 (—NH$^+$), 3600 to 3100 (—OH).

EXAMPLE 33

N-{[(7R)-3,4-Dimethoxybicyclo[4.2.0]octa-1,3,5-trien-7-yl]methyl}-3-(7-methoxy-1,2,4,5-tetrahydro-3H-3-benzazepin-3-yl)-N-methyl-3-oxopropan-1-amine hydrochloride Obtained in the same manner as the product of Example 13, but with replacement of the product of Step 3 of Example 1 by 3-acryloyl-7-methoxy-2,3,4,5-tetrahydro-1H-3-benzazepine, of the product of Preparation 2 by {[(7R)-3,4-dimethoxybicyclo[4.2.0]octa-1,3,5-trien-7-yl]methyl}methylamine, and of the toluene by THF.
Melting point (M.K.): 126-129° C.
Optical rotation: solvent: MeOH, C=0.0126 g/cm$^3$, T=20° C., L=589 nm, $\alpha_D$=+2.67

EXAMPLE 34

N-{[(7S)-3,4-Dimethoxybicyclo[4.2.0]octa-1,3,5-trien-7-yl]methyl}-3-(7-methoxy-1,2,4,5-tetrahydro-3H-3-benzazepin-3-yl)-N-methyl-3-oxopropan-1-amine hydrochloride Obtained in the same manner as the product of Example 13, but with replacement of the product of Step 3 of Example 1 by 3-acryloyl-7-methoxy-2,3,4,5-tetrahydro-1H-3-benzazepine, of the product of Preparation 2 by {[(7S)-3,4-dimethoxybicyclo[4.2.0]octa-1,3,5-trien-7-yl]methyl}methylamine, and of the toluene by THF.
Melting point (M.K.): 127-129° C.
Optical rotation: solvent: MeOH, C=0.01 g/cm$^3$, T=20° C., L=589 nm, $\alpha_D$=−2.7
IR (cm$^{-1}$): 1629 (C=O), 3000 to 1800 (—NH$^+$), 3500 (—OH) (weak).

EXAMPLE 35

7-({[3-(7,8-Dimethoxy-1,2,4,5-tetrahydro-3H-3-benzazepin-3-yl)-3-oxopropyl]amino}methyl)bicyclo[4.2.0]octa-1,3,5-trien-3-ol hydrochloride 10 g (38.3 mmol/0.95 eq.) of the product of Step 3 of Example 1, 6 g (40.2 mmol) of the product of Preparation 3 and 42 mg (0.2 mmol/0.05 eq.) of ruthenium trichloride are dissolved in 19 g of PEG 300. The solution is heated at 40° C.

for 4 hours. The reaction mixture is taken up in 600 mL of dichloromethane and is washed twice with 500 mL and then twice with 800 mL of water. The organic phase is dried over magnesium sulphate. After concentration, the residue is chromatographed over 500 g of silica (eluant:dichloromethane/ethanol/ammonia 95/5/0.5) to yield the expected product in the form of the base. 1 g of the pure base is made more solid in 9 mL of ethanol and is then converted into a salt using 1.1 eq. of 2N ethereal HCl in 9 mL of acetonitrile and is then finally recrystallised from a mixture of ethanol (27 mL) and of water (4 mL) to yield, after filtration and drying, the expected product in the form of the hydrochloride.

Melting point (M.K.): 212-215° C.

IR (cm$^{-1}$): 1633 (C=O), 3400 to 2400 (—NH$_2^+$/OH).

EXAMPLE 36

8-({[3-(7,8-Dimethoxy-1,2,4,5-tetrahydro-3H-3-benzazepin-3-yl)-3-oxopropyl]amino}methyl)bicyclo[4.2.0]octa-1,3,5-trien-3-ol Obtained in the same manner as the product of Example 35, but with replacement of the product of Preparation 3 by that of Preparation 4.

Melting point (M.K.): 193-195° C.

IR (cm$^{-1}$)): 1627 (C=O), 3700 to 2200 (—NH$_2^+$/OH).

EXAMPLE 37

N-[(Bicyclo[4.2.0]octa-1,3,5-trien-7-yl)methyl]3-(7,8-dimethoxy-1,2,4,5-tetrahydro-3H-3-benzazepin-3-yl)-3-oxopropan-1-amine hydrochloride Obtained in the same manner as the product of Example 35, but with replacement of the product of Preparation 3 by (bicyclo[4.2.0]octa-1,3,5-trien-7-yl-methyl)amine.

Melting point (M.K.): 189-193° C.

EXAMPLE 38

3-(7,8-Dimethoxy-1,2,4,5-tetrahydro-3H-3-benzazepin-3-yl)-N-{[4-methoxy-3-methyl-bicyclo[4.2.0]octa-1,3,5-trien-7-yl]methyl}-3-oxopropan-1-amine hydrochloride Obtained in the same manner as the product of Example 35, but with replacement of the product of Preparation 3 by that of Preparation 29.

Melting point (M.K.): 166-168° C.

EXAMPLE 39

3-(7,8-Dimethoxy-1,2,4,5-tetrahydro-3H-3-benzazepin-3-yl)-N-{[3-methoxy-4-methyl-bicyclo[4.2.0]octa-1,3,5-trien-7-yl]methyl}-3-oxopropan-1-amine hydrochloride Obtained in the same manner as the product of Example 35, but with replacement of the product of Preparation 3 by that of Preparation 30.

Melting point (M.K.): 211-214° C.

EXAMPLE 40

N-{[(7S)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl) N-methyl-4-oxobutan-1-amine hydrochloride Step 1: 4-(7,8-Dimethoxy 1,2,4,5-tetrahydro-3H-3-benzazepin-3-yl)-4-oxobutan-1-ol To 6.0 g (29 mmol) of 7,8-dimethoxy-2,3,4,5-tetrahydro-1H-3-benzazepine in 30 mL of THF, at 0° C., there are added, dropwise, over 15 minutes, 11.6 mL (29 mmol/1 eq.) of 2.6M n-butyl lithium solution in hexane. The mixture is then cooled to about −78° C. and poured dropwise, over 10 minutes, into a solution of 2.7 mL (34.8 mmol/1.2 eq.) of gamma-butyrolactone in 15 mL of THF. Stirring is carried out at −78° C. for 30 minutes and the temperature is then brought to −30° C. and held there for 1 hour; the temperature is then allowed to return to ambient temperature, where stirring is carried out for 48 hours. The mixture is poured into 75 mL of saturated aqueous ammonium chloride solution and is then extracted twice with 120 mL of ethyl acetate. The combined organic phases are washed with 150 mL of saturated aqueous sodium chloride solution, dried over magnesium sulphate and concentrated. The residue is taken up in 300 mL of ethyl acetate and washed twice with 75 mL 1M aqueous hydrochloric acid solution. The combined aqueous acid phases are re-extracted twice with 100 mL of dichloromethane. The organic phases are combined, dried over magnesium sulphate and concentrated to yield the desired product.

Step 2: 4-(7,8-Dimethoxy-1,2,4,5-tetrahydro-3H-3-benzazepin-yl)-4-oxobutanal 3.3 mL (46 mmol/6 eq.) of DMSO are added dropwise to 2.0 mL (23 mmol/3 eq.) of oxalyl chloride in 45 mL of dichloromethane, at −60° C. The mixture is brought to about −25° C. and a solution of 2.25 g (7.7 mmol) of the compound of Step 1 in 22 mL of dichloromethane is added dropwise. Stirring is carried out at −25° C. for 15 minutes; 6.5 mL (46 mmol/6 eq.) of triethylamine are then added dropwise and the mixture is allowed to return to ambient temperature gently. 75 mL of dichloromethane and 75 mL of water are then added; stirring, separation of the phases and washing of the organic phase successively with 75 mL of 1N aqueous hydrochloric acid solution, 75 mL of water, 75 mL of 1N aqueous sodium hydroxide solution and 75 mL of water are carried out. After drying over magnesium sulphate and concentration, the desired product is collected.

Step 3: N-{[(7S)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-N-methyl-4-oxobutan-1-amine hydrochloride At ambient temperature, 2.53 g (12.2 mmol) of {[(7S)-3,4-dimethoxybicyclo[4.2.0]octa-1,3,5-trien-7-yl]methyl}methylamine and 3.95 g (12.2 mmol/1 eq.) of the compound of Step 2 are mixed into 90 mL of dichloromethane. There are then added 3.88 g (18.3 mmol/1.5 eq.) of sodium triacetoxyborohydride and stirring is carried out at ambient temperature for 4 hours. There are then added 60 mL of 1N aqueous sodium hydroxide solution, followed by extraction twice with 150 mL of ethyl acetate. The combined organic phases are washed with 100 mL of water and then with 100 mL of saturated aqueous sodium chloride solution and are then dried over magnesium sulphate. After filtration and concentration, the residue is chromatographed over 300 g of silica (eluant:dichloromethane/ethanol/ammonia: 97/3/0.3) to yield the desired product in the form of the base. The latter is dissolved in 13 mL of isopropanol, converted into a salt using 0.67 mL of 4.8N ethanolic HCl and then recrystallised from 25 mL of ethyl acetate to yield the expected product.

Melting point (M.K.): 132-136° C.
Optical rotation: solvent: MeOH, C=0.012 g/cm$^3$, T=20° C., L=578nm, $\alpha_D$=+4.28.
IR (cm$^{-1}$): 3500 (OH), 2441 (NH$^+$), 1610 (C=O), 1278-1234-1204 (C—O—C), 865-845 (CH—Ar).

EXAMPLE 41

N-{[(7R)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-N-methyl-4-oxobutan-1-amine hydrochloride Obtained in the same manner as the product of Example 40 but with replacement, in Step 3, of the {[(7S)-3,4-dimethoxybicyclo[4.2.0]octa-1,3,5-trien-7-yl]methyl}methylamine by {[(7R)-3,4-dimethoxybicyclo[4.2.0]octa-1,3,5-trien-7-yl]methyl}methylamine (2 equivalents).

Melting point (M.K.): 106-137° C.

EXAMPLE 42

N-{[(7S)-3,4-Dimethoxybicyclo[4.2.0]octa-1,3,5-trien-7-yl]methyl}-3-(7,8-dimethoxy-1,2,4,5-tetrahydro-3H-3-benzazepin-3-yl)-4-oxobutan-1-amine hydrochloride Obtained in the same manner as the product of Example 40 but with replacement, in Step 3, of the {[(7S)-3,4-dimethoxybicyclo[4.2.0]octa-1,3,5-trien-7-yl]methyl}methylamine by {[(7S)-3,4-dimethoxybicyclo[4.2.0]octa-1,3,5-trien-7-yl]methyl}amine.

Melting point (M.K.): 169-171° C.
Optical rotation: solvent: MeOH, C=0.009 g/cm$^3$, T=20° C., L=589 nm, $\alpha_D$=–0.9.
IR (cm$^-$): 2719 (NH$_2^+$), 1630 (C=O), 1276-1202-1177 (C—O—C), 862-832-781 (CH—Ar).

EXAMPLE 43

7-({[3-(7,8-Dimethoxy-1,2,4,5-tetrahydro-3H-3-benzazepin-3-yl)-3-oxopropyl](methyl)amino}methyl)bicyclo[4.2.0]octa-1,3,5-trien-3-ol At ambient temperature, 3.2 g (7.8 mmol) of the product of Example 35, 6.4 mL (78mmol/10 eq.) of 37% aqueous formaldehyde solution and 0.98 g (15.6 mmol) of sodium cyanoborohydride are mixed into 145 mL of acetonitrile. Stirring is carried out for 1 hour 40 minutes at ambient temperature, followed by evaporation to dryness. The residue is taken up in 250 mL of water and the aqueous phase is extracted twice with 150 mL of dichloromethane. The combined organic phases are washed with water and dried over magnesium sulphate. After filtration, concentration and chromatography over 200 g of silica (eluant: dichloromethane/ethanol/ammonia: 95/5/0.5), the expected product is obtained in the form of the base.

As a result of converting the base, dissolved in acetonitrile, into a salt using ethereal HCl, the hydrochloride of the expected product is obtained.

Melting point (M.K.): 167-170° C.
IR (cm$^{-1}$): 3600 a 2000 (OH/NH$^+$), 1616 (C=O).

EXAMPLE 44

7-{[[3-(7,8-Dimethoxy-1,2,4,5-tetrahydro-3H-3-benzazepin-3-yl)-3-oxopropyl](methyl)amino]methyl}bicyclo[4.2.0]octa-1,3,5-trien-3-yl methylcarbamate hydrochloride To 0.7 g (1.65 mmol) of the compound of Example 43 in 30 mL of toluene, at ambient temperature, in an autoclave, there is added 0.2 mL (3.3 mmol/2 eq.) of methyl isocyanate and heating is carried out at 90° C. for 48 hours. After concentration, the residue is chromatographed over 130 g of silica (eluant: dichloromethane/ethanol/ammonia 95/5/0.5) to yield the expected product in the form of the base. The latter is dissolved in 6 mL of ethanol and treated with 0.5 mL of 3N ethanolic HCl to yield the expected product.

Melting point(M.K.): 185-188° C.

EXAMPLE 45

8-({[3-(7,8-Dimethoxy-1,2,4,5-tetrahydro-3H-3-benzazepin-3-yl)-3-oxopropyl](methyl)amino}methyl)bicyclo[4.2.0]octa-1,3,5-trien-3-ol Obtained in the same manner as the product of Example 43, but with replacement of the product of Example 35 by that of Example 36.

Melting point (M.K.): 201-205° C.
IR (cm$^{-1}$): 3071 (OH), 2672 (NH$^+$), 1634 (C=O), 1250-1228-1196 (C—O—C), 885-749-741 (CH—Ar).

EXAMPLE 46

8-{[[3-(7,8-Dimethoxy-1,2,4,5-tetrahydro-3H-3-benzazepin-3-yl)-3-oxopropyl](methyl)amino]methyl}bicyclo[4.2.0]octa-1,3,5-trien-3-yl methylcarbamate hydrochloride Obtained in the same manner as the compound of Example 44 but using the compound of Example 45 instead of the compound of Example 43.

Melting point (M.K.): 107-110° C.

EXAMPLE 47

7-{[[3-(7,8-Dimethoxy-1,2,4,5-tetrahydro-3H-3-benzazepin-3-yl)-3-oxopropyl](methyl)amino]methyl}bicyclo[4.2.0]octa-1,3,5-trien-3-yl dimethylcarbamate hydrochloride At ambient temperature, to 0.7 g (1.65 mmol) of the compound of Example 43 in 5 ml of pyridine, there are added, all at once, 0.3 mL (2.06 mmol/1.25 eq.) of triethylamine and then, dropwise, 0.2 mL (2.06 mmol/1.25 eq.) of dimethylcarbamoyl chloride. Stirring is carried out at ambient temperature overnight and the mixture is then concentrated. The residue is chromatographed over 130 g of silica (eluant: dichloromethane/ethanol/ammonia: 95/5/0.5) to yield the expected product in the form of the base. It is dissolved in 7 mL of ethanol and treated with 0.5 mL of 3N ethanolic HCl to yield the hydrochloride.

Melting point (M.K.): 176-180° C.

EXAMPLE 48

(−) enantiomer of 7-{[[3-(7,8-dimethoxy-1,2,4,5-tetrahydro-3H-3-benzazepin-3-yl)-3-oxopropyl](methyl)amino]methyl}bicyclo[4.2.0]octa-1,3,5-trien-3-yl dimethylcarbamate hydrochloride 1.9 g of the compound of Example 47 is separated by chromatography on a chiral phase; mobile phase: MeOH/DEA: 1000/1. The first product eluted corresponds to the expected product, which is converted into a salt using 3N ethanolic HCl.
Melting point (M.K.): 132-137° C.
Optical rotation: solvent: MeOH, C=0.012 g/cm$^3$, T=20° C., L=589 nm, $\alpha_D$=−6.72

EXAMPLE 49

(+) enantiomer of 7-{[[3-(7,8-dimethoxy-1,2,4,5-tetrahydro-3H-3-benzazepin-3-yl)-3-oxopropyl](methyl)amino]methyl}bicyclo[4.2.0]octa-1,3,5-trien-3-yl dimethylcarbamate hydrochloride The second product eluted in Example 48 corresponds to the expected product, which is converted into a salt under the same conditions as the product of Example 48.
Melting point (M.K.): 164-167° C.
Optical rotation: solvent: MeOH, C=0.01 g/cm$^3$, T=20° C., L=589 nm, $\alpha_D$=+7.15.

EXAMPLE 50

8-{[[3-(7,8-Dimethoxy-1,2,4,5-tetrahydro-3H-3-benzazepin-3-yl)-3-oxopropyl](methyl)amino]methyl}bicyclo[4.2.0]octa-1,3,5-trien-3-yl dimethylcarbamate hydrochloride Obtained in the same manner as the compound of Example 47 but using the compound of Example 45 instead of the compound of Example 43.
Melting point (M.K.): 108-112° C.

EXAMPLE 51

7-{[[3-(7,8-Dimethoxy-1,2,4,5-tetrahydro-3H-3-benzazepin-3-yl)-3-oxopropyl](methyl)amino]methyl}bicyclo[4.2.0]octa-1,3,5-trien-3-yl ethylcarbonate hydrochloride To 0.95 g (2.24 mmol) of the compound of Example 43 in 20 mL of dichloromethane, at ambient temperature, there is added, all at once, 0.33 mL (2.35 mmol/1.05 eq.) of triethylamine. The mixture is brought to about 0° C. and 0.23 mL (2.46 mmol/1.1 eq.) of ethyl chloroformate is poured in dropwise. Stirring is carried out at 0° C. for 1 hour 30 minutes and the temperature is then allowed to come back up to ambient temperature. The organic phase is washed twice with 20 mL of water and is dried over magnesium sulphate. After concentration, the residue (0.96 g) is chromatographed over 130 g of silica (eluant: dichloromethane/ethanol/ammonia 95/5/0.5) to yield the expected product in the form of a base, which when dissolved in 9 mL of ethanol and treated with 0.65 mL of 3N ethanolic HCl yields the hydrochloride.
Melting point (M.K.): 149-152° C.

EXAMPLE 52

8-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl methylcarbamate hydrochloride Step 1: tert-Butyl[3-(7,8-dimethoxy-1,2,4,5-tetrahydro-3H-3-benzazepin-3-yl-3-oxopropyl]-[(4-hydroxybicyclo[4.2.0]octa-1,3,5-trien-7-yl)methyl] carbamate At ambient temperature, 1.93 g (4.7 mmol) of the product of Example 36 and 1.03 g (4.7 mmol/1 eq.) of di-tert-butyl dicarbonate are mixed into 20 mL of dichloromethane. After stirring for 2 hours at ambient temperature, 50 mL of dichloromethane are added; washing twice with 40 mL of water and drying over magnesium sulphate are carried out. After concentration, the expected product is collected.
Melting point (M.K.): 150-154° C.

Step 2: 8-({(tert-Butoxycarbonyl-[3-(7,8-dimethoxy-1,2,4,5-tetrahydro-3H-3-benzazepin-3-yl)-3-oxopropyl]amino}methyl)bicyclo[4.2.0]octa-1,3,5-trien-3-yl) methylcarbamate The procedure is as in Example 44 but with replacement of the product of Example 43 by the product of Step 1 above.

Step 3: 8-{[[3-(7,8-Dimethoxy-1,2,4,5-tetrahydro-3H-3-benzazepin-3-yl)-3-oxopropyl]-amino]methyl}bicyclo[4.2.0]octa-1,3,5-trien-3-yl methylcarbamate hydrochloride 2.8 mL (8.4 mmol/10 eq.) of 3N HCl in ethyl acetate are added to 0.48 g (0.84 mmol) of the compound of Step 2 above dissolved in 8 mL of ethyl acetate. Stirring is carried out at ambient temperature overnight; the solid formed is then filtered off, rinsed with ethyl acetate and dried in vacuo to obtain the expected product.
Melting point (M.K.): 150-154° C.

EXAMPLE 53

8-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl dimethylcarbamate hydrochloride Step 1: 8-({(tert-Butoxycarbonyl-[3-(7,8-dimethoxy-1,2,4,5-tetrahydro-3H-3-benzazepin-3-yl)-3-oxopropyl]amino}methyl)bicyclo[4.2.0]octa-1,3,5-trien-3-yl) dimethylcarbamate The same procedure is used as for the compound of Example 47 but with replacement of the product of Example 43 by the product of Step 1 of Example 52.

Step 2: 8-{[[3-(7,8-Dimethoxy-1,2,4,5-tetrahydro-3H-3-benzazepin-3-yl)-3-oxopropyl]-amino]methyl}bicyclo[4.2.0]octa-1,3,5-trien-3-yl dimethylcarbamate hydrochloride To 0.93 g (1.6 mmol) of the compound of Step 1 dissolved in 9 mL of ethanol there are added 2.4 mL (7.2 mmol/4.5 eq.)

of 3N ethanolic HCl. Stirring is carried out at ambient temperature overnight; the solid formed is then filtered off and dried in vacuo to obtain the expected product.
Melting point (M.K.): 220-222° C.

EXAMPLE 54

7-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl dimethylcarbamate hydrochloride Step 1: 7-({(tert-Butoxycarbonyl-[3-(7,8-dimethoxy-1,2,4,5-tetrahydro-3H-3-benzazepin-3-yl)-3-oxopropyl]amino}methyl)bicyclo[4.2.0]octa-1,3,5-trien-3-yl) dimethylcarbamate 3.6 g (8.8 mmoles) of tert-butyl[3-(7,8-dimethoxy-1,2,4,5-tetrahydro-3H-3-benzazepin-3-yl)-3oxopropyl][(3-hydroxybicyclo[4.2.0]octa-1,3,5trien-7-yl)methyl]carbamate are dissolved in 50 mL of dichloromethane. At 0° C., 2.1 g (1.1 equivalents) of N,N-dimethylcarbamoyl chloride are added thereto. Stirring is carried out at 25° C. for 3 days. The mixture is poured into water, extracted with dichloromethane, separated off, dried over MgSO$_4$, filtered and evaporated to dryness. A residue is obtained is purified by flash chromatography over 70 g of silica (eluant: CH$_2$Cl$_2$/ethanol: 98/2 to 90/10) to yield the expected product.

Step 2: 7-{[[3(7,8-Dimethoxy-1,2,4,5-tetrahydro-3H-3-benzazepin-3-yl)-3-oxopropyl]amino]methyl}bicyclo[4.2.0]octa-1,3,5-trien-3-yl dimethylcarbamate hydrochloride 0.8 g (1.37 mmoles) of the product obtained in Step 1 is dissolved in 4 mL of ethanol and 2 mL of 3.2N ethanolic HCl are added. Heating is carried out at 60° C. for 2 hours. The mixture is allowed to cool to ambient temperature and stirring is carried out for 2 hours. A solid is filtered off, which is recrystallised from 6 mL of ethanol at reflux. The mixture is allowed to crystallise at 25° C., filtered and dried. The expected product is obtained in the form of a white solid.
Melting point (M.K.)=217-230° C.

EXAMPLE 55

7-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl 4-morpholinecarboxylate hydrochloride The same procedure is used as for the compound of Example 54, but with replacement, in Step 1, of the N,N-dimethylcarbamoyl chloride by morpholinyl-4-carbonyl chloride.
Melting point (M.K.)=217-220° C.

EXAMPLE 56

7-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl diethylcarbamate hydrochloride The same procedure is used as for the compound of Example 54, but with replacement, in Step 1, of the N,N-dimethylcarbamoyl chloride by N,N-diethylcarbamoyl chloride.
Melting point (M.K.)=197-200° C.

EXAMPLE 57

7-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl 1-pyrrolidinecarboxylate hydrochloride The same procedure is used as for the compound of Example 54, but with replacement, in Step 1, of the N,N-dimethylcarbamoyl chloride by pyrrolidinyl-1carbonyl chloride.
Melting point (M.K.)=220-222° C.

EXAMPLE 58

8-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl ethylcarbonate hydrochloride Step 1: 8-({(tert-Butoxycarbonyl-[3-(7,8-dimethoxy-1,2,4,5-tetrahydro-3H-3-benzazepin-3-yl)-3-oxopropyl]amino}methyl)bicyclo[4.2.0]octa-1,3,5-trien-3-yl) ethylcarbonate Obtained as for the synthesis of Example 51, but with replacement of the product of Example 43 by the tert-butyl [3-(7,8-dimethoxy-1,2,4,5-tetrahydro-3H-3-benzazepin-3-yl)-3-oxopropyl][(4-hydroxybicyclo[4.2.0]octa-1,3,5-trien-7-yl)methyl]carbamate obtained in Step 1 of Example 52.

Step 2: 8-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl ethylcarbonate hydrochloride To 2.55 g( 4.4 mmol) of the compound of Step 1 dissolved in 50 mL of ethyl acetate there are added 14.5 mL (44 mmol/10 eq.) of 3N HCl in ethyl acetate. Stirring is carried out at ambient temperature for 4 days; the solid formed is then filtered off, rinsed with ethyl acetate and dried in vacuo to obtain 2.15 g of a residue which is purified over silica (eluant: dichloromethane/ethanol/ammonia: 95/5/0.5). After converting to a salt using ethanolic HCl in ethanol, the expected product is obtained.
Melting point (M.K.): 164-167° C.

EXAMPLE 59

7-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl ethylcarbonate hydrochloride Obtained in the same manner as the product of Example 58 but with replacement, in Step 1, of the product of Step 1 of Example 52 by tert-butyl[3-(7,8-dimethoxy-1,2,4,5-tetrahydro-3H-3-benzazepin-3-yl)-3-oxopropyl][3-hydroxybicyclo[4.2.0]octa-1,3,5-trien-7-yl)methyl]carbamate.
Melting point (M.K.): 208-212° C.

EXAMPLE 60

8-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl acetate hydrochloride Step 1: 8-({(tert-Butoxycarbonyl-[3-(7,8-dimethoxy-1,2,4,5-tetrahydro-3H-3-benzazepin-3-yl)-3-oxopropyl]amino}methyl)bicyclo[4.2.0]octa-1,3,5-trien-3-yl) acetate To 3.25 g (6.4 mmol) of tert-butyl[3-(7,8-dimethoxy-1,2,4,5-tetrahydro-3H-3-benzazepin-3-yl)-3-oxopropyl][4-hydroxybicyclo[4.2.0]octa-1,3,5-trien-7-yl)methyl]carbamate obtained in Step 1 of Example 52 in 20 mL of dichloromethane, at ambient temperature, there is added, all at once, 0.33 mL (6.7 mmol/1.05 eq.) of triethylamine. The mixture is brought to about 0° C. and 0.45 mL (6.4 mmol/1 eq.) of acetyl chloride is poured in dropwise. Stirring is carried out 0° C. for 1 hour, and the mixture is allowed to come back up to ambient temperature. The organic phase is washed twice with 20 mL of water and dried over magnesium sulphate. After concentration, the residue is chromatographed over 200 g of silica (eluant: dichloromethane/ethyl acetate: 97/3) to yield the desired product.

Step 2: 8-{[[3-(7,8-Dimethoxy-1,2,4,5-tetrahydro-3H-3-benzazepin-3-yl)-3-oxopropyl]amino]methyl}bicyclo[4.2.0]octa-1,3,5-trien-3-yl acetate hydrochloride To 2.2 g (4.0 mmol) of the compound obtained in Step 1, dissolved in 45 mL of ethyl acetate, there are added 13.5 mL (40 mmol/10 eq.) of 3N HCl in ethyl acetate. Stirring is carried out at ambient temperature for 4 days and the reaction mixture is poured into 300 mL of ether; the solid formed is then filtered off, rinsed with ether and dried in vacuo to obtain a residue which is chromatographed over silica (eluant: dichloromethane/ethanol/ammonia: 95/5/0.5). After converting to a salt using ethanolic HCl in ethanol, the expected product is obtained in the form of the hydrochloride.

Melting point (M.K.): 176-179° C.

EXAMPLE 61

7-({[3-(7,8-Dimethoxy-1,2,4,5-tetrahydro-3H-3-benzazepin-3-yl)-3-oxopropyl]amino}methyl)bicyclo[4.2.0]octa-1,3,5-trien-3-yl hexahydrocyclopenta[c]pyrrole-2(1H)-carboxylate (cis compound)

Step 1: 7-({(tert-Butoxycarbonyl)-[3-(7,8-dimethoxy-1,2,4,5-tetrahydro-3H-3-benzazepin-3-yl)-3-oxopropyl]amino}methyl)bicyclo[4.2.0]octa-1,3,5-trien-3-yl hexahydrocyclopenta[c]pyrrole-2(1H)-carboxylate 1.5 g (2.94 mmol) of tert-butyl[3-(7,8-dimethoxy-1,2,4,5-tetrahydro-3H-3-benzazepin-3-yl)-3-oxopropyl][3-hydroxybicyclo[4.2.0]octa-1,3,5-trien-7-yl)methyl]carbamate, 4.1 mL of triethylamine and 2.37 g (11.74 mmol) of 4-nitrophenyl chloridocarbonate are dissolved in 210 mL of THF. Stirring is carried out at ambient temperature for 1 hour and then 0.65 g (5.87 mmol) of octahydropenta[c]pyrrole and 2.9 mL of triethylamine are added. After 2 hours at ambient temperature there is again added 0.65 g of octahydropenta[c]pyrrole and the mixture is left to stand at ambient temperature for 1 hour. The reaction mixture is diluted with 700 mL of ethyl acetate and is then washed with water, separated, dried over MgSO$_4$ and evaporated. The residue is chromatographed over silica (eluant: CH$_2$Cl$_2$/ethanol/NH$_4$OH: 99/1/0.1) to yield the expected product.

Step 2: 7-({[3-(7,8-Dimethoxy-1,2,4,5-tetrahydro-3H-3-benzazepin-3-yl)-3-oxopropyl]amino}methyl)bicyclo[4.2.0]octa-1,3,5-trien-3-yl hexahydrocyclopenta[c]pyrrole-2(1H)-carboxylate (cis compound)

The product obtained in Step 1 is dissolved in 10 volumes of ethanol and 10 volumes of 3N ethanolic HCl solution. Stirring is carried out at ambient temperature for 24 hours and the precipitate obtained, which corresponds to the expected product, is filtered off.

Melting point (M.K.): 214-217° C.

EXAMPLE 62

7-({[3-(7,8-Dimethoxy-1,2,4,5-tetrahydro-3H-3-benzazepin-3-yl)-3-oxopropyl]amino}methyl)bicyclo[4.2.0]octa-1,3,5-trien-3-yl 4,4-difluoro-1-piperidinecarboxylate Obtained as in example 61 but using, in Step 1, 4,4-difluoropiperidine instead of octahydropenta[c]pyrrole.

Melting point (M.K.): 212-216° C.

EXAMPLE 63

3-(7,8-Dimethoxy-1,2,4,5-tetrahydro-3H-3-benzazepin-3-yl)-N-[(3-isopropoxybicyclo[4.2.0]octa-1,3,5-trien-7-yl)methyl]-3-oxopropan-1-amine hemifumarate Step 1: tert-Butyl[3-(7,8-dimethoxy-1,2,4,5-tetrahydro-3H-3-benzazepin-3-yl)-3-oxopropyl]-[(3-hydroxybicyclo[4.2.0]octa-1,3,5-trien-7-yl)methyl]carbamate 3.6 g (8.8 mmoles) of the product of Example 35 are dissolved in 60 mL of dichloromethane. There are then added 2.1 g (1.1 equivalents) of di-tert-butyl dicarbonate and stirring is carried out at ambient temperature for 3 hours (until no more gas is evolved). The dichloromethane is evaporated off, drying in a vane pump vacuum is carried out and the expected product is obtained.

Step 2: tert-Butyl[3-(7,8-dimethoxy-1,2,4,5-tetrahydro-3H-3-benzazepin-3-yl)-3-oxopropyl]-[(3-isopropoxybicyclo[4.2.0]octa-1,3,5-trien-7-yl)methyl]carbamate 1.4 g (2.7 mmoles) of the product of Step 1 are dissolved in 15 mL of DMF. There are then added 740 mg (2 equivalents) of potassium carbonate, 160 mg (0.18 equivalent) of caesium carbonate and 0.54 mL (2 equivalents) of isopropyl iodide. Heating is then carried out at 40° C. for 24 hours. The DMF is evaporated off using a rotary evaporator. The residue obtained is then diluted with water and extracted with CH$_2$Cl$_2$. The organic phase is then dried over MgSO$_4$, filtered and evaporated to dryness. An oil is obtained which is purified by flash chromatography over 100 g of silica (eluant: CH$_2$Cl$_2$/ethyl acetate: 80/20) to yield the expected product in the form of a sticky meringue.

Step 3: 3-(7,8-Dimethoxy-1,2,4,5-tetrahydro-3H-3-benzazepin-3-yl)-N-[(3-isopropoxybicyclo[4.2.0]octa-1,3,5-trien-7-yl)methyl]-3-oxopropan-1-amine hemifumarate 1.1 g (1.99 mmoles) of the product of Step 2 are dissolved in 10 mL of ethanol. 14 mL (18 equivalents) of ethanolic HCl solution (2.6N) are then added. Stirring is carried out at ambient temperature overnight. A product crystallises out which is filtered off and dried to yield 800 mg of product. This solid material is dissolved in water; NaOH (1N) is added to bring the pH to 9; extraction with $CH_2Cl_2$, drying over $MgSO_4$, filtration and evaporation to dryness are carried out to obtain 650 mg of an oil. The latter is then purified by flash chromatography over 100 g of silica (eluant: $CH_2Cl_2$/ethanol/$NH_4OH$: 95/5/0.5). The expected product is obtained in the form of the base, which is dissolved in 10 mL of ethanol. 8.1 mL (1 equivalent) of a 2% fumaric acid solution in ethanol (M=0.172) are added. Stirring is carried out at ambient temperature for 30 minutes, and then evaporation to dryness is carried out. The residue obtained is crystallised from acetonitrile at 25° C. The crystals are filtered off; 314 mg of solid material are obtained which is recrystallised at reflux from acetonitrile. Filtration in the hot state is carried out and then crystallisation is allowed to take place for one hour at ambient temperature. The solid material is filtered off and dried to obtain the expected product in the form of white crystals.

Melting point (M.K.)=208-211° C.

EXAMPLE 64

2-{[((7S)-3,4-Dimethoxybicyclo[4.2.0]octa-1,3,5-trien-7-yl)-methyl]-(methyl)-amino}ethyl 7,8-dimethoxy-1,2,4,5-tetrahydro-3H-3-benzazepine-3-carboxylate hydrochloride Step 1: 7,8-Dimethoxy-1,2,4,5-tetrahydro-3H-3-benzazepine-3-carbonyl chloride To 1.2 mL (10 mmol/1 eq.) of diphosgene in 20 mL of dichloromethane, at about 0° C., there are added, dropwise, a solution of 3.55 g (20 mmol) of 7,8-dimethoxy-2,3,4,5-tetrahydro-1H-3-benzazepine in 22 mL of dichloromethane, and then 4.2 mL (30 mmol/1.5 eq.) of triethylamine. Stirring overnight at ambient temperature and then concentration are carried out. The residue is taken up in dichloromethane, washed with water and dried over magnesium sulphate to yield, after concentration, the desired product.

Step 2: 2-{[(3,4-Dimethoxybicyclo[4.2.0]octa-1,3,5-trien-7-yl)-methyl]-(methyl)-amino}ethyl 7,8-dimethoxy-1,2,4,5-tetrahydro-3H-3-benzazepine-3-carboxylate At ambient temperature, 0.23 g (5.7 mmol/1.25 eq.) of sodium hydride (60%) is cleaned with pentane and then 7 ml of THF are added. There is then added, dropwise, a solution of 1.14 g (4.5 mmol/1 eq.) of the compound of Preparation 25 in 7 mL of THF; stirring is carried out for 1 hour; 1.02 g (3.8 mmol/0.85 eq.) of the compound of Step 1 above are added in portions, and stirring is carried out overnight at ambient temperature. The reaction mixture is poured into 50 mL of 1N aqueous hydrochloric acid solution. Extraction with dichloromethane is carried out, and then the combined organic phases are washed with 1N sodium hydroxide solution and dried over magnesium sulphate. After filtration and concentration, the residue is chromatographed over 150 g of silica (eluant: dichloromethane/ethanol/ammonia: 98/2/0.2). The base thereby obtained is dissolved in isopropanol and converted into a salt using ethanolic HCl to yield the expected product.

Melting point (M.K.): 147-150° C.

Optical rotation: solvent: MeOH, C=0.01 g/cm$^3$, T=20° C., L=589 nm, $\alpha_D$=+7.1.

EXAMPLE 65

2-{[((7R)-3,4-Dimethoxybicyclo[4.2.0]octa-1,3,5-trien-7-yl)-methyl]-(methyl)-amino}ethyl 7,8-dimethoxy-1,2,4,5-tetrahydro-3H-3-benzazepine-3-carboxylate hydrochloride Obtained in the same manner as Example 64 but using, in Step 2, the product of Preparation 26 instead of the product of Preparation 25.

Melting point (M.K.): 144-147° C.

Optical rotation: solvent: MeOH, C=0.01 g/cm$^3$, T=20° C., L=589 nm, $\alpha_D$=−6.94.

EXAMPLE 66

N-{2-[{[(7S)-3,4-Dimethoxybicyclo[4.2.0]octa-1,3,5-trien-7-yl]methyl}(methyl)amino]ethyl}-7,8-dimethoxy-1,2,4,5-tetrahydro-3H-3-benzazepine-3-carboxamide methanesulphonate At ambient temperature, to 1.06 g (4.5 mmol) of the compound of Preparation 27 dissolved in 40 mL of dichloromethane there are added, all at once, 2.34 ml (13.4 mmol/3 eq.) of diisopropylethylamine and then, in portions, 1.02 g (3.8 mmol/0.85 eq.) of the compound of Step 1 of Example 64, and stirring is carried out overnight at ambient temperature. The reaction mixture is washed with water and concentrated. The residue is chromatographed over 140 g of silica (eluant: dichloromethane/ethanol/ammonia: 95/5/0.5). The purified product is converted into a salt using methanesulphonic acid in ethyl acetate and, after evaporation, is made more solid from ether to yield the expected product.

Melting point (M.K.): 65-85° C.

EXAMPLE 67

N-{2-[{[(7R)-3,4-Dimethoxybicyclo[4.2.0]octa-1,3,5-trien-7-yl]methyl}(methyl)amino]ethyl}-7,8-dimethoxy-1,2,4,5-tetrahydro-3H-3-benzazepine-3-carboxamide methanesulphonate Obtained in the same manner as Example 66 but using the product of Preparation 28 instead of the product of Preparation 27.

Melting point (M.K.): 65-85° C.

EXAMPLE 68

N-[(2,3-Dimethoxybicyclo[4.2.0]octa-1,3,5-trien-7-yl)methyl]-3-(7,8-dimethoxy-1,2,4,5-tetrahydro-3H-3-benzazepin-3-yl)-N-methyl-3-oxopropan-1-amine hydrochloride Obtained in the same manner as the product of Example 43, but with replacement of the product of Example 35 by that of Example 8.

Melting point (M.K.): 185-186° C.

EXAMPLE 69

N-[(2,3,4-Trimethoxybicyclo[4.2.0]octa-1,3,5-trien-7-yl)methyl]-3-(7,8-dimethoxy-1,2,4,5-tetrahydro-3H-3-benzazepin-3-yl)-N-methyl-3-oxopropan-1-amine fumarate Obtained in the same manner as the product of Example 43, but with replacement of the product of Example 35 by that of Example 9. Conversion to a salt is carried out using fumaric acid.

Melting point (M.K.): 158-160° C.

EXAMPLE 70

3-(7,8-Dimethoxy-1,2,4,5-tetrahydro-3H-3-benzazepin-3-yl)-N-[(5-methoxybicyclo[4.2.0]octa-1,3,5-trien-7-yl)methyl-N-methyl-3-oxopropan-1-amine hydrochloride Obtained in the same manner as the product of Example 43, but with replacement of the product of Example 35 by that of Example 10.

Melting point (M.K.): 130-132° C.

EXAMPLE 71

7-{[[3-(7,8-Dimethoxy-1,2,4,5-tetrahydro-3H-3-benzazepin-3-yl)-3-oxopropyl](methyl)amino]methyl}bicyclo[4.2.0]octa-1,3,5-trien-3-yl diethylcarbamate hydrochloride Obtained in the same manner as the product of Example 43, but with replacement of the product of Example 35 by that of Example 56.

Melting point (M.K.): 175-178° C.

EXAMPLE 72

7-{[[3-(7,8-Dimethoxy-1,2,4,5-tetrahydro-3H-3-benzazepin-3-yl)-3-oxopropyl](methyl)amino]methyl}bicyclo[4.2.0]octa-1,3,5-trien-3-yl 4-morpholinecarboxylate hydrochloride Obtained in the same manner as the product of Example 43, but with replacement of the product of Example 35 by that of Example 55.

Melting point (M.K.): 196-198° C.

EXAMPLE 73

7-{[[3-(7,8-Dimethoxy-1,2,4,5-tetrahydro-3H-3-benzazepin-3-yl)-3-oxopropyl](methyl)amino]methyl}bicyclo[4.2.0]octa-1,3,5-trien-3-yl 1-pyrrolidinecarboxylate hydrochloride Obtained in the same manner as the product of Example 43, but replacing the product of Example 35 by that of Example 57.

Melting point (M.K.): 174-177° C.

EXAMPLE 74

3-(7,8-Dimethoxy-1,2,4,5-tetrahydro-3H-3-benzazepin-3-yl)-N-{[3-methoxy-4-methyl-bicyclo[4.2.0]octa-1,3,5-trien-7-yl]methyl}-N-methyl-3-oxopropan-1-amine hydrochloride Obtained in the same manner as the product of Example 43, but with replacement of the product of Example 35 by that of Example 39.

Melting point (M.K.): 172-175° C.

EXAMPLE 75

8-{[[3-(7,8-Dimethoxy-1,2,4,5-tetrahydro-3H-3-benzazepin-3-yl)-3-oxopropyl](methyl)amino]methyl}bicyclo[4.2.0]octa-1,3,5-trien-3-yl ethylcarbonate hydrochloride Obtained in the same manner as the product of Example 43, but with replacement of the product of Example 35 by that of Example 58.

Melting point (M.K.): 156-159° C.

EXAMPLE 76

3-(7,8-Dimethoxy-1,2,4,5-tetrahydro-3H-3-benzazepin-3-yl)-N-{[4-methoxy-3-methyl-bicyclo[4.2.0]octa-1,3,5-trien-7-yl]methyl}-N-methyl-3-oxopropan-1-amine hydrochloride Obtained in the same manner as the product of Example 43, but with replacement of the product of Example 35 by that of Example 38.

Melting point (M.K.): 191-193° C.

EXAMPLE 77

N-[(Bicyclo[4.2.0]octa-1,3,5-trien-7-yl)methyl]-3-(7,8-dimethoxy-1,2,4,5-tetrahydro-3H-3-benzazepin-3-yl)-N-methyl-3-oxopropan-1-amine hydrochloride Obtained in the same manner as the product of Example 43, but with replacement of the product of Example 35 by that of Example 37.

Melting point (M.K.): 110-113° C.

EXAMPLE 78

7-({[3-(7,8-Dimethoxy-1,2,4,5-tetrahydro-3H-3-benzazepin-3-yl)-3-oxopropyl](methyl)amino}methyl)bicyclo[4.2.0]octa-1,3,5-trien-3-yl hexahydrocyclopenta[c]pyrrole-2(1H)-carboxylate (cis compound)

Obtained in the same manner as the product of Example 43, but with replacement of the product of Example 35 by that of Example 61.

Melting point (M.K.): 110-113° C.

EXAMPLE 79

2-({[(7S)-3,4-Dimethoxybicyclo[4.2.0]octa-1,3,5-trien-7-yl]methyl}[3-(7,8-dimethoxy-1,2,4,5-tetrahydro-3H-3-benzazepin-3-yl)-3-oxopropyl]-amino)-ethanol hydrochloride 1 g (2.2 mmol) of (7S)-N-[(3,4-dimethoxybicyclo[4.2.0]octa-1,3,5-trien-7-yl)methyl]-3-(7,8-dimethoxy-1,2,4,5-tetrahydro-3H-3-benzazepin-3-yl)-3-oxopropan-1-amine (obtained by returning the compound of Example 4 to the base), 0.4 g (3.3 mmol) of 1,4-dioxane-2,5-diol, 0.7 g (3.3 mmol) of sodium triacetoxyborohydride and 8 mL of methylene chloride are mixed together. After 45 minutes at ambient temperature, the reaction mixture is rendered basic with 10 mL of 1N sodium hydroxide solution and stirring is carried out for half an hour. The phases are separated, the aqueous phase is extracted twice with ethyl acetate, the organic phases are combined, washed with water and then with saturated NaCl solution and dried over $MgSO_4$. After evaporating off the solvent, a residue is isolated which is chromatographed over silica (eluant: $CH_2Cl_2$/EtOH/$NH_4OH$ 95/5/0.5) to yield the expected compound, which is converted into its hydrochloride using 2N ethereal HCl solution.

Melting point (M.K.): 75-79° C.

EXAMPLE 80

3-(7,8-Dimethoxy-1,2,4,5-tetrahydro-3H-3-benzazepin-3-yl)-N-{[3-(3-methoxypropoxybicyclo[4.2.0] octa-1,3,5-trien-7-yl]methyl}-3-oxopropan-1-amine hydrochloride Step A.: tert-Butyl[3-(7,8-dimethoxy-1,2,4,5-tetrahydro-3H-3-benzazepin-3-yl)-3-oxopropyl][3-hydroxybicyclo[4.2.0]octa-1,3,5-trien 7-yl)methyl]carbamate To 10 g (24.4 mmol) of 7-({[3-(7,8-dimethoxy-1,2,4,5-tetrahydro-3H-3-benzazepin-3-yl)-3-oxopropyl] amino}methyl)bicyclo[4.2.0]octa-1,3,5-trien-3-ol, obtained by returning the compound of Example 35 to the base, suspended in 120 mL of dichloromethane, at ambient temperature, there are added 20 mL of ethanol to partly dissolve the substance and then 6.4 g (29.3 mmol) of di-tert-butyl dicarbonate. Stirring is carried out at ambient temperature for 2 hours, 250 mL of dichloromethane are then added and washing is carried out twice using 200 mL of water. After drying the organic phase over magnesium sulphate, and then concentrating, there is obtained a residue which is purified by filtration over silica (eluant: dichloromethane/methanol 97/3).

Step B: 3-(7,8-Dimethoxy-1,2,4,5-tetrahydro-3H-3-benzazepin-3-yl)-N-{[3-(3-methoxypropoxybicyclo [4.2.0]octa-1,3,5-trien-7-yl]methyl}-3-oxopropan-1-amine hydrochloride At ambient temperature, 1.33 g (2.6 mmol) of the compound obtained in Step A, 43 mg (0.26 mmol) of potassium iodide, 1.27 g (3.9 mmol) of caesium carbonate and 0.40 mL (3.7 mmol) of methoxypropyl chloride are mixed into 2.6 mL of DMF, and then heating is carried out at 60° C. for 24 hours. The mixture is then poured into 50 mL of ice-cold water and extracted twice with 50 mL of ethyl acetate. The combined organic phases are washed with 30 mL of water, dried over magnesium sulphate and concentrated. The residue is chromatographed over 100 g of alumina (eluant: cyclohexane/ethyl acetate 75/25) to yield a compound which is dissolved in 8 mL of anhydrous ethanol and treated at ambient temperature with 1.55 mL (5.0 mmol) of 3.7N ethanolic HCl. Stirring is then carried out at ambient temperature for 45 hours. The solid that forms is filtered off to yield the desired compound in the form of the hydrochloride.

Melting point (M.K.): 155-159° C.

EXAMPLE 81

3-(7,8-Dimethoxy-1,2,4,5-tetrahydro-3H-3-benzazepin-3-yl)-N-{[3-(3-methoxypropoxybicyclo[4.2.0] octa-1,3,5-trien-7-yl]methyl}-N-methyl-3-oxopropan-1-amine hydrochloride At ambient temperature, 1.06 g (2.5 mmol) of 7-({[3-(7,8-dimethoxy-1,2,4,5-tetrahydro-3H-3-benzazepin-3-yl)3-oxopropyl](methyl)amino}methyl)bicyclo[4.2.0]octa-1,3,5-trien-3-ol (obtained by returning the compound of Example 43 to the base), 42 mg (0.25 mmol) of potassium iodide, 0.98 g (3.0 mmol) of caesium carbonate and 0.35 mL (3.25 mmol) of methoxypropyl chloride are mixed into 2.5 mL of DMF, and then heating is carried out at 50° C. for 3 days. The mixture is then poured into 50 mL of ice-cold water and extracted twice using 50 mL of ethyl acetate. The combined organic phases are washed with 30 mL of water, dried over magnesium sulphate and concentrated. The residue (1.21 g) is chromatographed over silica (eluant: dichloromethane/methanol 95/5) to yield 1.07 g of the desired compound in the form of the base. It is dissolved in 5 mL of acetonitrile and treated at ambient temperature with 1.2 mL of 2N ethereal HCl. Stirring is then carried out at ambient temperature for 2 hours. The solid that is formed is filtered off to yield 0.91 g of the desired compound in the form of the hydrochloride.

Melting point (M.K.): 142-147° C.

EXAMPLE 82

3-(7,8-Dimethoxy-1,2,4,5-tetrahydro-3H-3-benzazepin-3-yl)-N-{[3-(3-methoxyethoxybicyclo[4.2.0] octa-1,3,5-trien-7-yl]methyl}-3-oxopropan-1-amine hydrochloride The procedure is as in Example 80 but using, in Step B, methoxyethyl chloride instead of methoxypropyl chloride.

Melting point (M.K.): 159-170° C.

EXAMPLE 83

3-(7,8-Dimethoxy-1,2,4,5-tetrahydro-3H-3-benzazepin-3-yl)-N-{[3-(3-methoxyethoxybicyclo[4.2.0] octa-1,3,5-trien-7-yl]methyl}-N-methyl-3-oxopropan-1-amine hydrochloride The procedure is as in Example 81 but using methoxyethyl chloride instead of methoxypropyl chloride.

Melting point (M.K.): 129-131° C.

EXAMPLE 84

2-{[[7-({[3-(7,8-Dimethoxy-1,2,4,5-tetrahydro-3H-3-benzazepin-3-yl)-3-oxopropyl]amino}methyl)bicyclo[4.2.0]octa-1,3,5-trien-3-yl]oxy}-N-methylacetamide hydrochloride.

Step A: ([7-({(tert-Butoxycarbonyl)[3-(7,8-dimethoxy-1,2,4,5-tetrahydro-3H-3-benzazepin-3-yl)-3-oxopropyl]amino}methyl)bicyclo[4.2.0]octa-1, 3,5-trien-3-yl)oxy]carboxylic acid ethyl ester 6.8 g (13.3 mmol) of the compound obtained in Step A of Example 80, 2.3 g (16.6 mmol) of potassium carbonate and 2.21 mL (20.0 mmol) of ethyl bromoacetate are mixed into 13.3 mL of DMF. The reaction mixture is stirred at ambient temperature for 25 hours, is then poured into 250 mL of ice-cold water and is extracted twice with 150 mL of ethyl acetate. The combined organic phases are washed with 100 mL of water, dried over magnesium sulphate and concentrated to yield the desired compound.

Step B: tert-Butyl[3-(7,8-dimethoxy-1,2,4,5-tetrahydro-3H-3-benzazepin-3-yl)-3-oxopropyl]-({3-[2-(methylamino)2-oxoethoxy]bicyclo[4.2.0]octa-1,3,5-trien-7-yl}methyl)-carbamate At ambient temperature, 2.6 g (4.4 mmol) of the compound obtained in Step A above, dissolved in 20 mL of ethanol, are mixed with 20 mL of 40% aqueous monomethylamine solution. Stirring is carried out at ambient temperature for 3 days and then concentration is carried out. The residue is taken up successively with toluene, with ethanol, and then with toluene and concentrated to yield the desired product.

Step C: 2-{[7-({[3-(7,8-Dimethoxy-1,2,4,5-tetrahydro-3H-3-benzazepin-3-yl)-3-oxopropyl]-amino}methyl)bicyclo[4.2.0]octa-1,3,5-trien-3-yl]oxy}-N-methylacetamide hydrochloride At ambient temperature, 2.63 g (4.5 mmol) of the compound obtained in Step B above are mixed into 120 mL of ethanol together with 25 mL of 3.7N ethanolic HCl. After stirring for 1 day at ambient temperature, the solid formed is filtered off, rinsed with ethanol and with ether and dried in vacuo to obtain the desired compound in the form of the hydrochloride.
Melting point (M.K.): 145-146° C.

EXAMPLE 85

2-{[7-({[3-(7,8-Dimethoxy-1,2,4,5-tetrahydro-3H-3-benzazepin-3-yl)-3-oxopropyl](methyl)amino}methyl)bicyclo[4.2.0]octa-1,3,5-trien-3-yl]oxy}-N-methylacetamide hydrochloride At ambient temperature, to 0.83 g (1.72 mmol) of the compound obtained in Step C of Example 84, dissolved in 32 mL of acetonitrile, there are added, all at once, 1.4 mL (17.2 mmol) of 37% aqueous formaldehyde solution and then 0.22 g (3.44 mmol) of sodium cyanoborohydride. After stirring for 45 minutes at ambient temperature, concentration is carried out and the residue is taken up in 30 mL of water; the aqueous phase is extracted twice with 30 mL of dichloromethane; the organic phases are combined, washed with 30 mL of water and dried over magnesium sulphate. After concentration, the residue is chromatographed over silica (eluant: dichloromethane/ethanol/ammonia 95/5/0.5) to yield the desired compound in the form of the base.
The base is dissolved in 4 mL of ethanol and treated with 0.3 mL of 3.7N ethanolic HCl. After stirring for 1 hour at ambient temperature, the solid formed is filtered off, rinsed with ethanol and dried in vacuo to obtain the desired compound in the form of the hydrochloride.
Melting point (M.K.): 147-153° C.

Pharmacological Study

EXAMPLE 86

Effect of compounds on the spontaneous beating rate of the right atrium in the rat Male WISTAR rats weighing from 325 to 375 g are anaesthetised by ip injection of pentobarbital sodium (30 mg/kg). The heart is rapidly excised and placed in a physiological solution at 4° C. which contains (in mM): NaCl 120.3, KCl 4.8, $CaCl_2$ 2.5, $KH_2PO_4$ 1.0, $MgSO_4$ 1.3, $NaHCO_3$ 24.2, glucose 11.1, Ca-EDTA 0.016, and which is oxygenated (carbogene 95% $O_2$+5% $CO_2$), pH 7.4. The right atrium (RA), which beats spontaneously, is isolated, placed in a basin, thermostatically controlled at 35° C., containing 20 ml of physiological solution and connected to an isometric tension sensor (model IT-25, EMKA Technologies, Paris, France). The initial tension is set at 0.4 g. The spontaneous beating rate is measured by IOX software (EMKA Technologies, Paris, France). Preparations whose spontaneous beating rate is not between 200 and 300 beats per minute are excluded.

The compounds are dissolved daily at $10^{-2}$M. The following dilutions are stored in ice over the duration of the experiment.

After stabilisation for 30 minutes, the compound under test is added to the medium in cumulative manner every 15 minutes (4 concentrations). The reductions in beating rate are expressed as a percentage relative to the initial rate. The concentration that reduces the initial beating rate by 30% (IC30) is calculated and expressed in terms of molarity (μM).

| Results | |
| --- | --- |
| Compound | $IC_{30}$ (μM) |
| Example 3a | 1.3 |
| Example 4 | 1.4 |
| Example 7 | 1.7 |
| Example 14 | 1 |
| Example 22 | 0.8 |
| Example 23 | 1.4 |
| Example 27 | 1.2 |
| Example 28 | 1.2 |
| Example 29 | 0.4 |
| Example 34 | 1.3 |
| Example 44 | 0.8 |
| Example 46 | 0.5 |
| Example 47 | 0.6 |
| Example 48 | 0.5 |
| Example 50 | 0.5 |
| Example 53 | 1.8 |
| Example 54 | 0.8 |
| Example 71 | 1.8 |
| Example 73 | 2.4 |
| Example 74 | 1.0 |
| Example 76 | 1.6 |
| Example 78 | 2.0 |

The above Table shows that the compounds of the invention reduce cardiac pacemaker activity directly.

EXAMPLE 87

Pharmaceutical composition

Formula for the preparation of 1000 tablets each containing 10 mg of active ingredient:

| | |
| --- | --- |
| Compound of one of Examples 1 to 85 | 10 g |
| Hydroxypropylcellulose | 2 g |
| Wheat starch | 10 g |
| Lactose | 100 g |
| Magnesium stearate | 3 g |
| Talc | 3 g |

The invention claimed is:

1. A compound selected from those of formula (I):

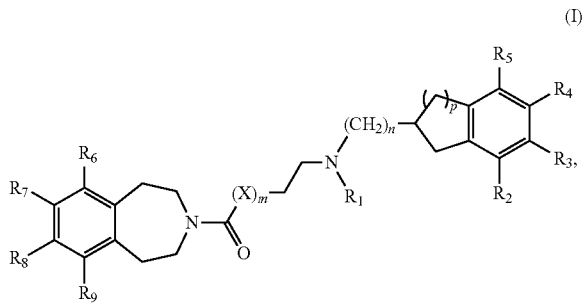

wherein:
- $R_1$ represents hydrogen, $C_3$-$C_7$cycloalkyl, benzyl or linear or branched $C_1$-$C_6$alkyl, wherein the alkyl group may be saturated or unsaturated and may be optionally substituted by a hydroxy or $C_3$-$C_7$cycloalkyl group or by one or more halogen atoms,
- $R_2$, $R_3$, $R_4$ and $R_5$, which may be the same or different, each represent hydrogen; hydroxy; methyl; —$OSO_2R_{10}$; —$OCOR_{10}$; or linear or branched, saturated or unsaturated $C_1$-$C_6$alkoxy which may be optionally substituted by a methoxy or —(CO)—$NR_{12}R'_{12}$ group, or $R_2$ and $R_3$, or $R_3$ and $R_4$, or $R_4$ and $R_5$ together form —O—$(CH_2)_q$—O—, —O—CH=CH—O— or —O—CH=CH—,
- $R_6$, $R_7$, $R_8$ and $R_9$, which may be the same or different, each represent hydrogen or linear or branched, saturated or unsaturated $C_1$-$C_6$alkoxy, or $R_6$ and $R_7$, or $R_7$ and $R_8$, or $R_8$ and $R_9$ together form —O—$(CH_2)_q$—O—,
- $R_{10}$ represents linear or branched $C_1$-$C_6$alkoxy, $NR_{11}R'_{11}$ or linear or branched $C_1$-$C_6$alkyl which is optionally substituted by one or more halogen atoms,
- $R_{11}$ and $R'_{11}$, which may be the same or different, each represent hydrogen or linear or branched $C_1$-$C_6$alkyl, or $R_{11}$ and $R'_{11}$ together with the nitrogen atom carrying them form a monocyclic or bicyclic, 5- to 8-membered, nitrogen-containing heterocycle optionally containing another hetero atom selected from O and N, said heterocycle being optionally substituted by one or more halogen atoms,
- $R_{12}$ and $R'_{12}$, which may be the same or different, each represent hydrogen or linear or branched $C_1$-$C_6$alkyl,
- X represents O, NH or $CH_2$,
- m and p, which may be the same or different, each represent 0 or 1,
- n and q, which may be the same or different, each represent 1 or 2, its optical isomers and addition salts thereof with a pharmaceutically acceptable acid.

2. The compound of claim 1, wherein $R_1$ represents hydrogen or linear or branched $C_1$-$C_6$alkyl.

3. The compound of claim 1, wherein $R_1$ represents $C_3$-$C_7$cycloalkyl or cycloalkylalkyl wherein the cycloalkyl moiety has from 3 to 7 carbon atoms and the alkyl moiety has from 1 to 6 carbon atoms and is linear or branched.

4. The compound of claim 1, wherein $R_2$, $R_3$, $R_4$ and $R_5$, which may be the same or different, each represent hydrogen, linear or branched, saturated or unsaturated $C_1$-$C_6$alkoxy or —$OCOR_{10}$ wherein $R_{10}$ represents $NR_{11}R'_{11}$.

5. The compound of claim 1, wherein $R_6$, $R_7$, $R_8$ and $R_9$, which may be the same or different, each represent hydrogen or linear or branched, saturated or unsaturated $C_1$-$C_6$alkoxy.

6. The compound of claim 1, wherein m represents 0.

7. The compound of claim 1, wherein m represents 1 and X represents $CH_2$.

8. The compound of claim 1, wherein p represents 0.

9. The compound of claim 1, wherein p represents 1.

10. The compound of claim 1, wherein $R_1$ represents hydrogen or linear or branched $C_1$-$C_6$alkyl, $R_2$, $R_3$, $R_4$ and $R_5$, which may be the same or different, each represent hydrogen or linear or branched, saturated or unsaturated $C_1$-$C_6$alkoxy, $R_6$, $R_7$, $R_8$ and $R_9$, which may be the same or different, each represent hydrogen or linear or branched, saturated or unsaturated $C_1$-$C_6$alkoxy, m represents 0, n represents 1 and p represents 0.

11. The compound of claim 1 which is selected from:
- N-{[3,4-dimethoxybicyclo[4.2.0]octa-1,3,5-trien-7-yl]methyl}-3-(7,8-dimethoxy-1,2,4,5-tetrahydro-3H-3-benzazepin-3-yl)-N-methyl-3-oxopropan-1-amine, its optical isomers, and also addition salts thereof with a pharmaceutically acceptable acid;
- N-{[3,4-dimethoxybicyclo[4.2.0]octa-1,3,5-trien-7-yl]methyl}-3-(7,8-dimethoxy-1,2,4,5-tetrahydro-3H-3-benzazepin-3-yl)-3-oxopropan-1-amine, its optical isomers, and also addition salts thereof with a pharmaceutically acceptable acid;
- N-[2-(5,6-dimethoxy-2,3-dihydro-1H-inden-2-yl)methyl]-3-(7,8-dimethoxy-1,2,4,5-tetrahydro-3H-3-benzazepin-3-yl)-3-oxopropan-1-amine, and also addition salts thereof with a pharmaceutically acceptable acid;
- N-{[3,4-dimethoxybicyclo[4.2.0]octa-1,3,5-trien-7-yl]methyl}-3-(7,8-dimethoxy-1,2,4,5-tetrahydro-3H-3-benzazepin-3-yl)-N-methyl-4-oxobutan-1-amine, its optical isomers, and also addition salts thereof with a pharmaceutically acceptable acid;
- N-{[3,4-dimethoxybicyclo[4.2.0]octa-1,3,5-trien-7-yl]methyl}-3-(7,8-dimethoxy-1,2,4,5-tetrahydro-3H-3-benzazepin-3-yl)-4-oxobutan-1-amine, its optical isomers, and also addition salts thereof with a pharmaceutically acceptable acid; and
- 7-{[[3-(7,8-dimethoxy-1,2,4,5-tetrahydro-3H-3-benzazepin-3-yl)-3-oxopropyl]-(methyl)amino]methyl}bicyclo[4.2.0]octa-1,3,5-trien-3-yl dimethylcarbamate, its optical isomers and addition salts thereof with a pharmaceutically acceptable acid.

12. A pharmaceutical composition comprising as active ingredient a compound of claim 1, in combination with one or more pharmaceutically acceptable, inert, non-toxic excipients or carriers.

13. A method for treating a condition selected from ischaemic cardiopathies, heart failure, ventricular or supraventricular rhythm disturbances, stable angina, unstable angina, myocardial infarction, post infarction, arterial hypertension, diabetes and hypercholesterolaemia, comprising the step of administering to a living animal body a therapeutically effective amount of a compound of claim 1.

14. The method of claim 13, wherein the living animal body is a human.

* * * * *